(12) United States Patent
Sojka et al.

(10) Patent No.: US 8,383,160 B2
(45) Date of Patent: Feb. 26, 2013

(54) COMPOSITIONS COMPRISING SOLID PARTICLES ENTRAPPED IN COLLAPSED POLYMERIC MICROSPHERES, AND METHODS OF MAKING THE SAME

(75) Inventors: Milan F. Sojka, Corman, NY (US); Phillip Cummins, Livingston, NJ (US); Christina G. Fthenakis, Dix Hills, NY (US); Jean Harry Xavier, Holbrook, NY (US)

(73) Assignee: ELC Management, LLC, New York, NY (US)

( * ) Notice: Subject to any disclaimer, the term of this patent is extended or adjusted under 35 U.S.C. 154(b) by 0 days.

(21) Appl. No.: 13/227,573

(22) Filed: Sep. 8, 2011

(65) Prior Publication Data
US 2012/0045579 A1  Feb. 23, 2012

Related U.S. Application Data

(62) Division of application No. 12/138,742, filed on Jun. 13, 2008, now abandoned.

(60) Provisional application No. 61/014,235, filed on Dec. 17, 2007.

(51) Int. Cl.
 *A61K 9/14* (2006.01)
 *A61Q 1/02* (2006.01)
 *A61Q 17/00* (2006.01)
 *A61Q 17/04* (2006.01)
 *A61Q 19/00* (2006.01)

(52) U.S. Cl. .......... 424/497; 424/59; 424/489; 424/490; 977/773

(58) Field of Classification Search .................. None
See application file for complete search history.

(56) References Cited

U.S. PATENT DOCUMENTS

| | | |
|---|---|---|
| 1,964,682 A | 6/1934 | Ayers |
| 3,615,972 A * | 10/1971 | Morehouse et al. ............ 156/79 |
| 3,864,181 A | 2/1975 | Wolinski et al. |
| 4,006,223 A | 2/1977 | Chitulescu et al. |
| 4,044,176 A | 8/1977 | Wolinski et al. |
| 4,366,827 A | 1/1983 | Madrange et al. |
| 4,397,799 A | 8/1983 | Edgren et al. |
| 4,513,106 A | 4/1985 | Edgren et al. |
| 4,671,955 A | 6/1987 | Palinczar |
| 4,722,943 A | 2/1988 | Melber et al. |
| 4,962,170 A | 10/1990 | Chromecek et al. |
| 5,219,561 A | 6/1993 | Gagnebien et al. |
| 5,223,250 A | 6/1993 | Mitchell et al. |
| 5,314,683 A | 5/1994 | Schlossman |
| 5,393,809 A | 2/1995 | Gueret |
| 5,451,610 A * | 9/1995 | Krzysik .......................... 424/63 |
| 5,452,584 A * | 9/1995 | Diggs .............................. 62/64 |
| 5,593,680 A | 1/1997 | Bara et al. |
| 5,635,109 A | 6/1997 | Otsuka |
| 5,733,531 A | 3/1998 | Mitchnick et al. |
| 5,733,572 A | 3/1998 | Unger et al. |
| 5,747,010 A | 5/1998 | Geesin et al. |
| 5,755,998 A | 5/1998 | Yamazaki et al. |
| 5,817,299 A | 10/1998 | Manirazman |
| 5,851,538 A | 12/1998 | Froix et al. |
| 5,955,091 A | 9/1999 | Hansenne |
| 6,096,331 A | 8/2000 | Desai et al. |
| 6,146,649 A | 11/2000 | Hansenne |
| 6,254,877 B1 | 7/2001 | DeLaPoterie et al. |
| 6,313,181 B1 | 11/2001 | Cohen |
| 6,592,882 B2 | 7/2003 | George et al. |
| 6,753,002 B2 | 6/2004 | George et al. |
| 6,814,959 B1 | 11/2004 | Müller et al. |
| 2001/0007710 A1* | 7/2001 | Liu et al. ..................... 428/207 |
| 2003/0108492 A1 | 6/2003 | Chaudhuri |
| 2003/0124071 A1* | 7/2003 | Candau et al. .................. 424/59 |
| 2003/0215394 A1 | 11/2003 | Short et al. |
| 2004/0141933 A1* | 7/2004 | Luo et al. ........................ 424/64 |
| 2004/0161395 A1 | 8/2004 | Patil et al. |
| 2004/0228886 A1 | 11/2004 | Ding et al. |
| 2005/0112154 A1 | 5/2005 | Giroud et al. |
| 2005/0129759 A1* | 6/2005 | Sojka ........................... 424/469 |
| 2005/0208005 A1 | 9/2005 | Giroud |
| 2005/0244349 A1 | 11/2005 | Chaudhuri et al. |
| 2005/0249682 A1* | 11/2005 | Buseman-Williams et al. .............................. 424/59 |

(Continued)

FOREIGN PATENT DOCUMENTS
| | | |
|---|---|---|
| CA | 2330863 | 11/1999 |
| DE | 2521003 | 8/1976 |

(Continued)

OTHER PUBLICATIONS

Azko Nobel. "Expancel® Microspheres." Apr. 2001, 2 printed pages.*

(Continued)

*Primary Examiner* — Frederick Krass
*Assistant Examiner* — Isaac Shomer
(74) *Attorney, Agent, or Firm* — Cynthia R. Miller

(57) ABSTRACT

The present invention relates to method for modifying or treating solid particles which includes the steps of:
 (a) forming a gelled mixture by mixing either simultaneously or sequentially in any order: (1) hollow microspheres each comprising a deformable polymeric shell having entrapped therein an expandable fluid, (2) a polar organic solvent capable of swelling but not dissolving the polymeric shells of the hollow microspheres, and (3) solid particles, wherein micro-channels are formed in the swelled polymer shells to allow entry of the solid particles into the hollow microspheres and exit of the expandable fluid therefrom, thereby forming microspheres that each comprises a collapsed polymeric shell in a gelled state and has one or more of said solid particles entrapped therein;
 (b) removing the expandable fluid and the polar organic solvent from the gelled mixture; and
 (c) coating the microspheres thus-produced with a film-forming material to form a liquid-impermeable membrane thereon.

25 Claims, 6 Drawing Sheets

U.S. PATENT DOCUMENTS

| | | |
|---|---|---|
| 2006/0153889 A1 | 7/2006 | Friel et al. |
| 2007/0071978 A1 | 3/2007 | Sojka et al. |
| 2009/0155371 A1 | 6/2009 | Sojka et al. |

FOREIGN PATENT DOCUMENTS

| | | |
|---|---|---|
| EP | 0056219 | 7/1982 |
| EP | 0112807 | 7/1984 |
| EP | 0585239 | 9/1998 |
| FR | 2 700 952 | 8/1994 |
| GB | 2237574 | 5/1991 |
| JP | 60-184004 | 9/1985 |
| JP | 3025436 | 2/1991 |
| JP | 3-267140 | 11/1991 |
| JP | 10-338612 | 12/1998 |
| JP | 11-100311 | 4/1999 |
| JP | 2000-072645 | 3/2000 |
| JP | 2005-154649 | 6/2005 |
| KR | 2002-0079131 | 10/2002 |
| WO | WO00/41528 | 7/2000 |
| WO | WO2007/038404 | 5/2007 |

OTHER PUBLICATIONS

Ahamad, M.; Flexible Vinyl Resiliency Property Enhancement With Hollow Thermoplastic Microspheres; Journal of Vinyl & Additive Tech; vol. 7; No. 3; pp. 156-161; Sep. 2001.

An Introduction to Expancel Microspheres; An Introduction; Akzo Nobel; www.Expancel.com; No Publication Date Available; 2004.

PCT International Search Report; International Application No. PCT/US2006/037207; Completion Date: Jan. 24, 2007; Date of Mailing: Jan. 24, 2007.

PCT Written Opinion of the International Searching Authority; International Application No. PCT/US2006/037207; Completion Date: Jan. 24, 2007; Date of Mailing: Jan. 24, 2007.

Takatsugu Yoshioka; New ingredients and application for ultraviolet-ray protection; Fragrance Journal, Japan; vol. 27; No. 5; pp. 62-70; May 1999, (Eng. Trans).

Brown, et al.; Bicyclic monoterpene diols stimulate release of nitric oxide from skin cells, increase microcirculation, and elevate skin temperature; Nitric Oxide Biology and Chemistry; Nitric Oxide 15; pp. 70-76; Feb. 2006.

University of North Carolina Eshelman School of Pharmacy. "Factors Influencing the Solubility of Drugs." http://pharmlabs.unc.edu/labs/solubility/structure.htm, accessed Sep. 6, 2011. 3 printed pages.

Supplementary European Search Report; EP08863316; Completion Date: Sep. 28, 2011; Date of Mailing: Oct. 11, 2011.

Optisol™; Advanced UV Protection . . . ; Company Phamphlet; Croda Chemicals Europe Ltd.; 2006.

Creations Couleurs; Eospoly®; http://www.creationscouleurs.com/en/products/eospoly.html; 2004.

PCT International Search Report; International Application No. PCT/US08/083607; Completion Date: Jun. 16, 2009; Date of Mailing: Jun. 16, 2009.

PCT Written Opinion of the International Searching Authority, or The Declaration; International Application No. PCT/US08/083607; Completion Date: Jun. 16, 2009; Mailing Date: Jun. 16, 2009.

PCT International Search Report; International Application No. PCT/US2009/052683; Completion Date: Feb. 22, 2010; Date of Mailing: Feb. 24, 2010. (Related Application : U.S. Appl. No. 12/507,145-08.22).

PCT Written Opinion of the International Searching Authority, or The Declaration; International Application No. PCT/US2009/052683; Completion Date: Feb. 22, 2010; Date of Mailing: Feb. 24, 2010. (Related Application : U.S. Appl. No. 12/507,145-08.22).

Maier, Harald, et al.; Change of Ultraviolet Absorbance of Sunscreens by Exposure to Solar-Simulated Radiation; The Journal of Investigative Dermatology; vol. 117, No. 2; pp. 256-262; 2001.

Lee, Wilson A., et al.; Multicomponent polymer coating to block photocatalytic activity of $TiO_2$ nanoparticles; Chemical Communications 45; pp. 4815-4817; 2007.

PCT International Search Report; International Application No. PCT/US2011/020655; Completion Date: Sep. 21, 2011; Date of Mailing: Sep. 21, 2011.

PCT Written Opinion of the International Searching Authority; International Application No. PCT/US2011/020655; Completion Date: Sep. 21, 2011; Date of Mailing: Sep. 21, 2011.

* cited by examiner

COMPOSITIONS COMPRISING SOLID PARTICLES ENTRAPPED IN COLLAPSED POLYMERIC MICROSPHERES, AND METHODS OF MAKING THE SAME

CROSS-REFERENCE TO RELATED APPLICATIONS

This is a divisional application of U.S. patent application Ser. No. 12/138,742, filed Jun. 13, 2008, now abandoned which claims priority from U.S. Provisional Patent Application Ser. No. 61/014,235, filed Dec. 17, 2007.

FIELD OF THE INVENTION

The present invention relates to topical compositions comprising stabilized particulate components, as well as methods of making the same.

BACKGROUND OF THE INVENTION

Cosmetic or topical compositions typically comprise one or more particulate components, such as, for example, pigments or dyes, fillers, thickeners, sunscreen agents, and the like. Such particulate components are often insoluble in the respective solvent or carrier system and if so remain dispersed or suspended in the cosmetic or topical compositions.

However, whenever there are changes in the pH and temperature in the surrounding environment, the dispersed or suspended particles may agglomerate with one another and precipitate out of the composition. Further, the smaller the particle size, the larger the active surface area, and the more susceptible such particulate components are toward adverse interactions or interference with other ingredients or components in the cosmetic or topical compositions, which may destabilize the cosmetic or topical compositions or reduce the overall performance thereof.

There is therefore a continuing need for treating or modifying the particulate components of cosmetic or topical compositions in order to eliminate or mitigate the above-described drawbacks and improve the overall stability of the compositions without adversely affecting the chemical and physical properties of the particulate components.

There is also a need for improving the chemical and/or physical properties of the particulate components through surface treatment or modification.

SUMMARY OF THE INVENTION

In one aspect, the present invention relates to a topical composition comprising a dispersion of microspheres in a cosmetically or pharmaceutically acceptable carrier, wherein each of the microspheres comprises a collapsed polymeric shell having entrapped therein one or more solid particles.

In another aspect, the present invention relates to a microsphere comprising a collapsed polymeric shell having entrapped therein one or more solid particles, while the collapsed polymeric shell is further coated with a liquid-impermeable membrane.

In yet another aspect, the present invention relates to a topical sunscreen composition comprising a dispersion of microspheres in a cosmetically or pharmaceutically acceptable carrier, while each of the microspheres comprises a collapsed polymeric shell having entrapped therein one or more solid particles that comprise titanium dioxide, zinc oxide, or a combination thereof.

In a still further aspect, the present invention relates to a method for modifying or treating solid particles, comprising:
(a) forming a gelled mixture by mixing either simultaneously or sequentially in any order: (1) hollow microspheres each comprising a deformable polymeric shell having entrapped therein an expandable fluid, (2) a polar organic solvent capable of swelling but not dissolving the polymeric shells of the hollow microspheres, and (3) solid particles, wherein micro-channels are formed in the swelled polymer shells to allow entry of the solid particles into the hollow microspheres and exit of the expandable fluid therefrom, thereby forming microspheres that each comprises a collapsed polymeric shell in a gelled state and has one or more of said solid particles entrapped therein;
(b) removing the expandable fluid and the polar organic solvent from the gelled mixture; and
(c) coating the microspheres with a film-forming material to form a liquid-impermeable membrane thereon.

Other aspects and objectives of the present invention will become more apparent from the ensuing description, examples, and claims.

DETAILED DESCRIPTION OF THE INVENTION

Figure 1:
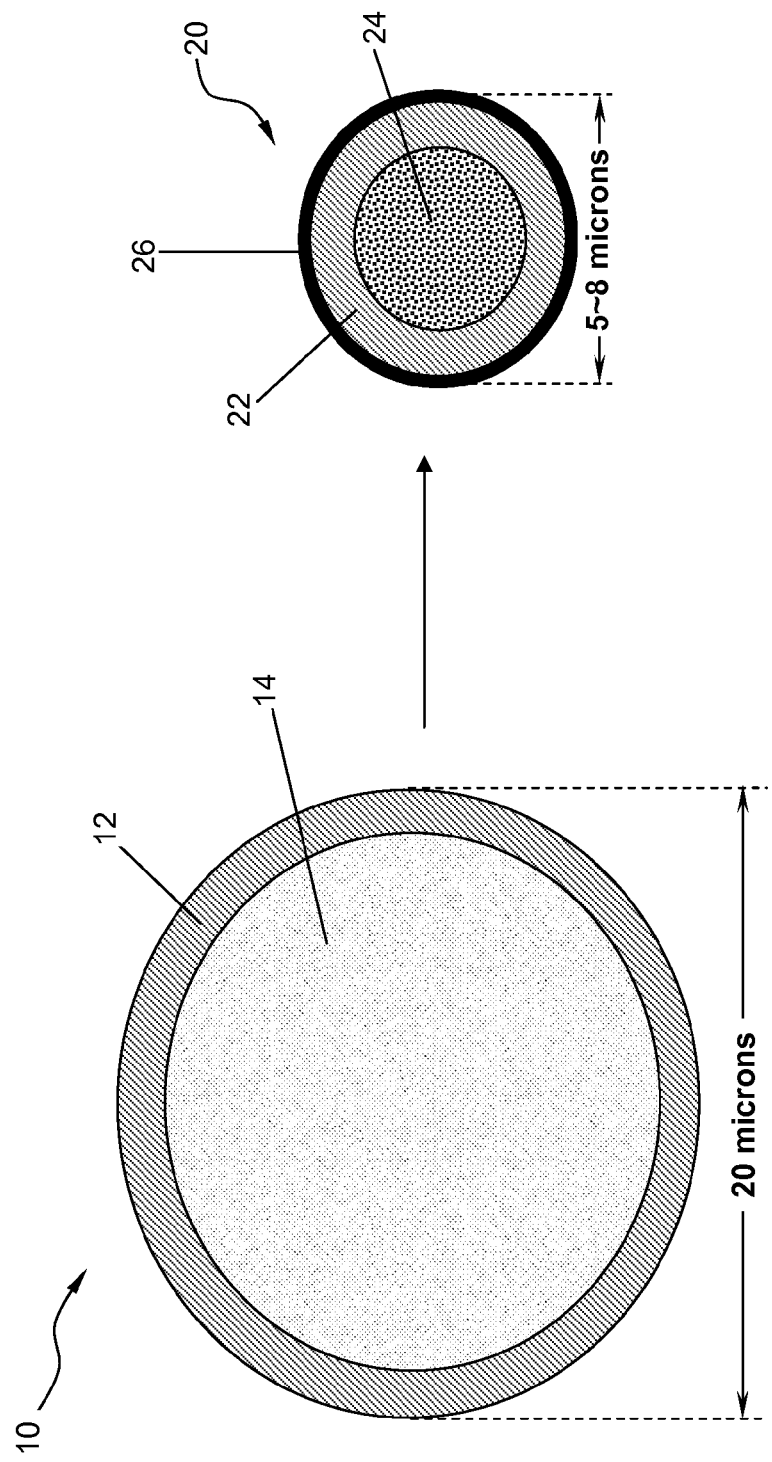
FIG. 1 are schematic views of: (1) an untreated hollow microsphere with a deformable polymeric shell and an expandable fluid entrapped therein, and (2) a microsphere containing a collapsed polymeric shell with solid particles entrapped therein and a liquid-impermeable membrane coated thereover, which is formed by processing the untreated hollow microsphere according to one embodiment of the present invention.

The present invention provides stabilized particulate components that are useful in cosmetic or topical compositions, as well as methods for stabilizing particulate components. Specifically, the particulate components are entrapped in polymeric microspheres having an average particle size that is at least 10 times, preferably 20 times, more preferably 50 times, and most preferably 100 times, larger than the average particle size of the particulate components themselves. Each of the microspheres comprises a collapsed polymeric shell having entrapped therein one or more solid particles. Preferably, the physical and/or chemical properties of the entrapped solid particles pertaining to or associated with their desired activities in the cosmetic or topical compositions are not adversely affected, while the significantly larger microspheres provide improved structural and spatial stability.

Entrapment of the solid particles is achieved in the present invention by first providing hollow microspheres with deformable polymeric shells having encapsulated therein an expandable fluid, which are then mixed with, either sequentially in any order or simultaneously, a polar organic solvent capable of swelling but not dissolving the polymeric shells of the hollow microspheres and solid particles to be entrapped. A gelled mixture is thereby formed, which contains microspheres with polymeric shells in a gelled state, which are sufficiently swelled so as to have micro-channels or through-holes formed therein to allow entry of the solid particles into the microspheres. Such micro-channels or through-holes in the swelled polymeric shells of the microspheres also allow exit of the expandable fluid from the microspheres, thereby causing immediate collapse or implosion of the polymeric shells and entrapping the solid particles inside the microspheres. Subsequently, the expandable fluid and the polar organic solvent are removed from the gelled mixture. Preferably but not necessarily, a film-forming material is coated over the collapsed polymeric shells to form a liquid-impermeable membrane thereon, which functions to isolate the collapsed polymeric shells of the microspheres from any solvent in the surrounding environment that may swell or otherwise affect the structural integrity of such polymeric shells. In this manner, the solid particles can be securely entrapped inside the microspheres with little or no risk of leaking out.

The hollow microspheres as initially provided (i.e., before mixing with the solid particles and the polar organic solvent) are preferably expandable hollow polymeric microspheres, each of which contains a deformable polymeric shell that is gas-tight and has enclosed or encapsulated therein an expandable fluid. Upon heating, the enclosed or encapsulated fluid can expand volumetrically to apply pressure on the interior wall of the deformable polymeric shell. At the same time, the elevated temperature may cause the polymeric shell to soften, thereby allowing the entire microsphere to expand in a manner similar to a balloon.

The deformable polymeric shells of the hollow microspheres can be formed of any synthetic or natural crosslinked or un-crosslinked polymer. If the polymer is crosslinked, it is preferred that it is weakly crosslinked. Preferably, but not necessarily, the polymeric shells of the hollow microspheres comprise at least one synthetic polymer obtained by polymerization of one or more ethylenically unsaturated monomers to form homopolymers or copolymers of ethylenically unsaturated monomers or copolymers of ethylenically unsaturated monomers and one or more organic groups. Examples of ethylenically unsaturated monomers that may be suitable include, for example, vinylidene chloride, vinyl chloride, acrylonitrile, acrylic acid and its corresponding $C_1$-$C_{20}$ aliphatic or aromatic esters, methacrylic acid and its corresponding $C_1$-$C_{20}$ aliphatic or aromatic esters, acrylamide, methacrylamide, vinyl pyrrolidone, alkenes such as styrene, ethylene, propylene, butylene, methylpentene, 1,3-butadiene, and the like. The polymeric shells of the hollow microspheres may also be formed of suitable synthetic polymers, such as polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers of the above-listed polymers. In a particularly preferred embodiment, the deformable polymeric shells of the hollow microspheres are formed of a copolymer of vinylidene chloride, acrylonitrile, and/or methyl methacrylate.

The expandable fluid inside the hollow microspheres of the present invention can be any suitable gas (e.g., air or nitrogen) or volatile liquid hydrocarbons (e.g., isobutane or isopentane). Preferably, the expandable fluid is selected from the group consisting of air, nitrogen, isobutane, and isopentane. More preferably, the expandable fluid is either isobutane or isopentane.

Hollow microspheres having deformable polymeric shells comprised of a copolymer of vinylidene chloride, acrylonitrile, and methylmethacrylate with an expandable fluid comprised of isobutane or isopentane are commercially available under the trade name of EXPANCEL® from Expancel, Inc. at Duluth, Ga. The EXPANCEL® hollow microspheres are available in various forms, e.g., dry, wet, unexpanded or pre-expanded. Both the dry, unexpanded microspheres (EXPANCEL® DU) and the dry, expanded microspheres (EXPANCEL® DE) can be used in the present invention for entrapping and stabilizing the solid particles. The EXPANCEL® DU microspheres have an average particle size ranging from about 6 to about 40 microns and a density of about 1-1.3 g/cm$^3$. The EXPANCEL® DE microspheres have an average particle size ranging from about 20 to about 150 microns and a density of about 0.03-0.07 g/cm$^3$.

Any suitable polar organic solvent that can sufficiently swell, but not dissolve, the polymeric shells of the hollow microspheres can be used to treat the hollow microspheres described hereinabove. Examples of polar organic solvents that can be used in practice of the present invention include, but are not limited to: dimethylformamide, dimethylchloride, trichloroethylene (TCE), chloroform, methanol, ethanol, isopropanol, acetone, ethyl acetate, butyl acetate, and methyl ethyl ketone (MEK). Acetone is most preferred in the present invention. Upon mixing with untreated hollow microspheres, the polar organic solvent can swell the polymeric shells of the hollow microspheres significantly and thereby convert the gas-tight polymeric shells of the untreated hollow microspheres into a gelled state with multiple micro-channels or pores formed therein.

The solid particles to be entrapped and stabilized according to the present invention can be any particulate components that are commonly used in cosmetic or topical compositions, which include, but are not limited to: mineral pigments and fillers such as, for example, talc, kaolin, mica, bismuth oxychloride, chromium hydroxide, barium sulfate, polymethylmethacrylates (PMMA), boron nitride, nylon beads, polymeric powders (e.g., BPD 500 powders comprised of hexamethylene diisocyanate/trimethylol hexyllactone crosspolymer and silica that is commercially available from Kobo Products, Inc. at South Plainfield, N.J.), silica, silica beads, lakes (e.g., aluminum or calcium lake), metal oxides (e.g., black, yellow or blue iron oxide, chromium oxide, zinc oxide, and titanium dioxide), physical and chemical sunscreen agents, and any other organic and inorganic powders or particles. Preferably, but not necessarily, the solid particles are comprised of a material capable of generating free oxygen radicals, and more preferably a metal oxide such as zinc oxide or titanium dioxide. The solid particles can be of any regular or irregular shape, such as, for example, spherical, cubic, cylindrical, planar, fibrous, and the like. The average particle size of the solid particles as used in the present invention should be significantly smaller than that of the hollow microspheres, so that the solid particles can readily enter and be entrapped by the hollow microspheres. Preferably, the average particle size of the solid particles is less than 1 micron, more preferably from about 0.001 micron to about 0.1 micron, and most preferably from about 0.01 to about 0.05 micron. A particular preferred example of the solid particles includes a manganese modified titanium dioxide particle commercially available under the trade name of Optisol™ from Croda, Inc. at Edison, N.J.

The hollow microspheres, the polar organic solvent and the solid particles as described hereinabove are mixed together, either simultaneously or sequentially, to form a gelled mixture. If mixed sequentially, the ingredients can be added and mixed in any suitable order. For example, the hollow microspheres and the solid particles can be blended together first, followed by addition of the polar organic solvent to form a slurry. For another example, the solid particles can be dispensed in the polar organic solvent first, and then mixed with the hollow microspheres. For still another example, the hollow microspheres can be added into the polar organic solvent to form a gel first, and the solid particles are then added into the gel. In any event, all the ingredients are well mixed until a homogenous mixture is formed. The weight ratio between the hollow microspheres and the polar organic solvent is preferably from about 1:3 to about 1:100 and more preferably from about 1:20 to about 1:50, so that the polymeric shells of the hollow microspheres can be sufficiently swelled by the solvent. The weight ratio between the solid particles and the hollow microspheres can range widely from about 1:10 to about 100:1, preferably from about 2:3 to about 10:1, and more preferably from about 1:1 to about 2:1.

Because the polymeric shells of hollow microspheres are comprised of a non-crosslinked or weakly crosslinked polymer, as mentioned hereinabove, the polar organic solvent molecules, which are sufficiently small in comparison with the polymeric molecules, can enter between the polymeric chains, interrupt the intermolecular bonds between neighboring polymeric chains, and pull the polymeric chains apart from each other. Consequently, the polymeric shells of the hollow microspheres are swelled by the polar organic solvent, so as to form a gelled mixture that contains porous networks of interconnected polymeric chains spanning or dispersed throughout the volume of the polar organic solvent. The polymeric shells of the microspheres in such a gelled state are not longer gas-tight, but have become porous, i.e., with sufficiently large micro-channels therein to allow entry of the solid particles into the sufficiently swelled microspheres. At the same time, the expandable fluid exit from such microspheres through the micro-channels, causing the gelled polymeric shells to collapse or implode and resulting in shrunk microspheres with significantly decreased overall volume. In this manner, the solid particles become entrapped within the collapsed polymeric shells of the shrunk microspheres.

Such shrunk microspheres have an average particle size ranging from about 1 to 15 microns, and more from about 5 microns to about 8 microns. The shrunk microspheres are significantly smaller in size than the untreated hollow microspheres. Further, the shrunk microspheres are no longer hollow, but are now filled by the solid particles with little or no empty space left therein. At the same time, the polymeric shells of the microspheres remain in a gelled state, i.e., swelled by the polar organic solvent. It is important to note that the shrunk microspheres of the present invention, although morphologically and volumetrically modified by the gelling process, remain as separate particles in the gelled mixture with little or no coalescence. Subsequent drying of the gelled mixture therefore forms fine free-flowing powders, which contain microspheres with well-defined surface boundaries and minimum clumping or agglomeration.

The gelling process as described herein is fundamentally different from the well known sol gel process. In a typical sol-gel process, metal alkoxide and metal chloride precursors are first solubilized to form a solution (sol) and then undergo hydrolysis and polycondensation reactions to form a colloid system composed of solid particles dispersed in a solvent, followed by evolvement toward the formation of an inorganic network containing a liquid phase (gel), which can be dried to remove the liquid phase from the gel thus forming a porous material. In contrast, the gelling process of the present invention does not involve hydrolysis or polycondensation reactions, and it forms a network of water-insoluble polymeric chains dispersed in the polar organic solvent.

The gelled mixture as described hereinabove can be subjected to de-gassing, in which the gelled mixture is placed under a reduced pressure or vacuum conditions, so as to remove the expandable fluid from the gelled mixture. Subsequently, a second solvent that is miscible with the polar organic solvent previously used for swelling/gelling the microspheres can be added into the de-gassed gelled mixture with sufficient agitation, so as to "quench" the gelled mixture by separating the swelled microspheres from one another. For example, when the polar organic solvent is acetone, the second solvent can be water, which is miscible with acetone. Due to the immiscibility between the polar organic solvent and the second solvent, the microspheres become more spatially separated from one another and therefore more dispersed. Such further dispersion of the microspheres functions to minimize the risk of coalescence during subsequent drying of the gelled mixture. Further separation of the microspheres can be achieved by a filtration or centrifugation step, which is optional for the purpose of the present invention.

After the de-gassing and quenching steps, both the polar organic solvent and the second solvent are preferably removed from the gelled mixture to form dry, free-flowing powders containing the microspheres with the solid particles entrapped therein. Removal of the polar organic solvent and the second solvent can be readily achieved by various separation and/or drying techniques well known in the art, such as decantation, centrifugation, filtration, solvent extraction, air drying, vacuum drying, freeze drying, spray drying, fluid bed drying, supercritical fluid drying, and the like. The polymeric shells, which have been previously swelled by the polar organic solvent and become porous with micro-channels extending therethrough, shrink significantly and lose their porosity after being dried. In other words, the micro-channels formed through the swelled polymeric shells of the microspheres during the gelling step close up after the drying step, thereby securely entrapping the solid particles inside the microspheres. To minimize agglomeration between the dried microspheres, the resulting powders can be further subject to milling and sieving through one or more screens.

In order to eliminate or minimize the potential risk of the entrapped solid particles leaking out of the dried microspheres, the resulting dry, free-flowing powders are coated or otherwise surface-treated with a film-forming material, which forms a liquid-impermeable membrane over each of the dried microspheres. In this manner, the dried microspheres are sealed from solvents in the surrounding environment, which may potentially re-swell the polymeric shells of the microspheres and cause the entrapped solid particles to leak out.

Any material capable of forming a liquid-impermeable membrane, either hydrophilic or hydrophobic, can be used in the present invention. Suitable materials include film-forming materials such as natural or synthetic homo- or co-polymers comprised of ethylenically unsaturated monomers including acrylic acid, methacrylic acid or their $C_1$-$C_{10}$ alkyl esters, ethylene, propylene, or vinylpyrrolidones; silicone gums, which are organosiloxanes generally having a viscosity ranging from about 200,000 to 10,000,000 centipoise at room temperature; animal, vegetable, silicone or mineral waxes; organic ester or hydrocarbon oils, or silicone resins such as trimethylsiloxy silicate or polymethylsilsesquioxane; cellulosic polymers; fatty acids (e.g. fatty carboxylic acids having from about 6 to 40 carbon atoms that may be liquid, solid or semi-solids at room temperature), fatty alcohols (e.g. alcohols having from 6 to 50 carbon atoms that may be liquid, solid, or semi-solid at room temperature), and inorganic materials. Preferably, but not necessarily, the film-forming material comprises an alkyl silicone polymer or more specifically a fatty alkylmethylsiloxane, such as cetyl dimethicone, stearyl dimethicone, or behenyl dimethicone, or other modified siloxanes, such as polyoxyalkylenated silicones typically referred to as dimethicone copolyol or cetyl dimethicone copolyol. For example, a polymethylhydrogensiloxane, which is commercially available from Dow Corning Corporation at Midland, Mich. under the trade name of Dow Corning® MH 1107 fluid, can be used as the film-forming material in the present invention. This polymethylhydrogensiloxane material is a colorless silicone liquid that can be heat cured in the presence of a catalyst (e.g., zinc octoate, iron octoate, dibutyl tin dilaurate, and tin octoate) to form a solid, liquid-impermeable membrane comprised of cross-linked dimethicone over the microspheres of the present invention. For another example, silicone copolymers commercialized by Dow Corning under the trade name of BIO-PSA, which are formed by reacting a siloxane resin with a diorganosiloxane, can also be used as film-forming materials in the present invention to form the liquid-impermeable membrane over the microspheres. Among various types of BIO-PSA materials available from Dow Corning, the Dow Corning® 7-4404, 7-4405, and 7-4411 fluids (containing trimethylated silica treated with dimethylsiloxane and dispersed in a cosmetically acceptable solvent, such as octamethyltrisiloxane, isododecane, or decamethyltetrasiloxane) are particularly preferred.

The resulting microspheres with the solid particles entrapped therein and the liquid-impermeable membrane coated thereover may have an average particle size ranging from about 1 to about 50 microns, more preferably from about 1 to about 15 microns, and most preferably from about 5 to about 8 microns, as determined by a Malvern Particle Size Analyzer, available from Malvern Instrument at Worcestershire, UK. The entrapped solid particles may account for from about 10% to about 90% of the total weight of the resulting microspheres, more preferably 30% to about 75% of the total weight, and most preferably from about 40% to about 60% of the total weight. The polymeric shells may account for from about 5% to about 75% of the total weight of the resulting microspheres, more preferably from about 10% to about 60% of the total weight, and most preferably from about 30% to about 50% of the total weight. The liquid-impermeable coating material may account for from about 1% to about 30% of the total weight of the resulting microspheres, more preferably from about 5% to about 20% of the total weight, and most preferably from about 10% to about 15% of the total weight.

FIG. 1 illustratively shows schematic views of an untreated hollow microsphere 10 and a microsphere 20 according to one embodiment of the present invention, which is formed by processing the untreated hollow microsphere 10 according to the method described hereinabove. Specifically, the untreated hollow microsphere 10 includes a gas-tight and deformable polymeric shell 12 with an expandable fluid 14 entrapped therein. The diameter of the untreated hollow microsphere 10 is approximately 20 microns. In contrast, the microsphere 20 of the present invention includes a collapsed polymeric shell 22 with solid particles 24 entrapped therein and a liquid-impermeable membrane 24 coated thereover. The diameter of the microsphere 20 is significantly smaller than that of the untreated hollow microsphere 10 and approximately ranges from about 5 to about 8 microns.

Figure 2:
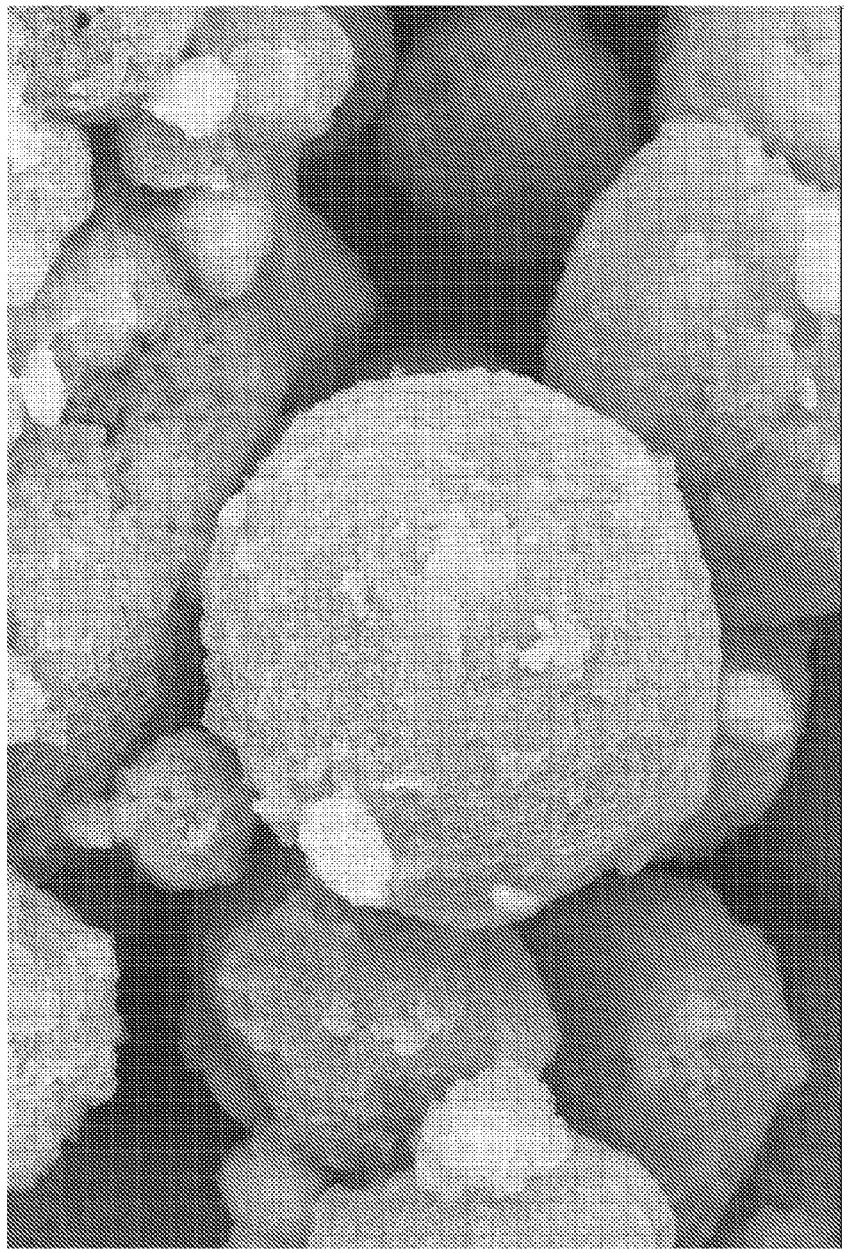
FIG. 2 is a Scanning Electron Microscopy (SEM) image of microspheres formed by entrapping $TiO_2$ particles in EXPANCEL® microspheres, according to one embodiment of the present invention.

FIG. 2 shows a Scanning Electron Microscopy (SEM) image of collapsed EXPANCEL® microspheres with $TiO_2$ particles entrapped therein, which were formed according to the treatment method of the present application as described hereinabove. The SEM picture was taken at 15K× magnification.

When formulated into topical compositions, the microsphere-entrapped solid particles of the present invention provide various advantages and benefits that are not available in their un-encapsulated or "naked" counterparts. For example, because the entrapped solid particles are sealed off from potentially destabilizing or degrading active ingredients in the topical composition, they are significantly more stable than their un-encapsulated or "naked" counterparts. Further, if the solid particles are potentially capable of degrading or otherwise interfering with other active ingredients in the topical composition, the entrapment of such solid particles functions to reduce the interference or degradation and improves the overall stability of the topical composition. Entrapment by microspheres may also alter the hydrophobicity or hydrophilicity of the solid particles and allow such solid particles to be formulated into aqueous, oil or silicone phases that are typically incompatible with un-encapsulated or "naked" solid particles. It is important to note that the desired chemical and/or physical properties of the solid particles should remain substantially unaffected by the entrapment described hereinabove.

Because the microspheres of the present invention are formed by entrapping solid particles in pre-formed, hollow polymeric microspheres that are subsequently collapsed during the entrapment process, rather than conventional in situ formation of polymeric coatings or matrixes around the solid particles, the microspheres of the present invention are characterized by substantially more uniform particle sizes and reduced agglomeration between the microspheres. Further, the entrapment process of the present invention allows the solid particles to be entrapped into microspheres that are many times larger in size than the solid particles themselves (e.g., 10×, 20×, 50×, or 100×) within a relatively short period of time, while the conventional in situ coating or matrix-forming process is very time-consuming and can only form microspheres of limited sizes.

Although applicable to any cosmetic or topical ingredient or component of solid, particulate form, it is believed that the present invention is particularly useful for stabilizing solid particles capable of generating free oxygen radicals without adversely affecting the desired properties of such particles, while at the same time eliminating any potential interaction between such free-oxygen-radical-generating solid particles and other cosmetic or topical ingredients in the formulations that are susceptible to oxidative decomposition or degradation. For example, solid particles formed of certain metal oxides, such as zinc oxide and titanium dioxide, are known to have photoprotective characteristics and can therefore be used as physical sunscreen agents. However, such metal oxide particles in their "naked" or untreated states are known to release free oxygen radicals upon exposure to UV light. Such free oxygen radicals are strong oxidants, which are capable of oxidatively degrading other cosmetic or topical components in the surrounding environments, such as, for example, organic dyes or organic sunscreen agents that are typically susceptible to oxidative decomposition or degradation. Entrapment of such free-oxygen-radical-generating metal oxide particles by the microspheres of the present invention has been shown to effectively eliminate or reduce formation or release of the free oxygen radicals from such particles upon UV exposure, without adversely affecting the sunscreen properties of such metal oxide particles. Consequently, the microsphere-entrapped metal oxide particles of the present invention can be ready used with organic compounds that are known to be susceptible to oxidative decomposition or degradation to form topical or cosmetic compositions with significantly improved overall stability and prolonged shelf life.

The microsphere-entrapped solid particles of the present invention can be added directly to any pharmaceutically or cosmetically acceptable carrier to form a cosmetic or topical composition. For purpose of the present invention, pharmaceutically or cosmetically acceptable carriers are substances that are biologically compatible with human skin and can be used to formulate active ingredients described hereinabove and/or hereinafter into a cream, gel, emulsion, liquid, suspension, powder, nail coating, skin oil, or lotion that can be topically applied. In the case where the cosmetically acceptable carrier is in the form of an emulsion, it may contain from about 0.1 to 99%, preferably from about 0.5 to 95%, more preferably from about 1 to 80% by weight of the total composition of water and from about 0.1 to 99%, preferably from about 0.1 to 80%, more preferably from about 0.5 to 75% by weight of the total composition of oil. In the case where the composition is anhydrous it may comprise from about 0.1 to 90 wt % of oil and from about 0.1 to 75 wt % of other ingredients such as pigments, powders, non-aqueous solvents (such as mono-, di-, or polyhydric alcohols, etc. In the case where the composition is in the form of an aqueous based gel, solution, or suspension, it may comprise from about 0.1 to 99 wt % of water and from about 0.1 to 75 wt % of other ingredients such as botanicals, non-aqueous solvents, etc.

Suitable components of the pharmaceutically or cosmetically acceptable carrier include, but are not limited to: moisturizing agents, astringent agents, chelating agents, sequestrants, emulsifiers/surfactants, emollients, preservatives, stabilizers, abrasives, adsorbents, thickeners, gellants, solidifying/structuring agents, anti-caking agents, anti-foaming agents, pH buffering/adjusting agents, binders, film formers, humectants, pigments, opacifiers, essential oils, fragrances, and aromatic compounds. The pharmaceutically or cosmetically acceptable carrier or carriers can be present in the topical or cosmetic composition of the present invention at an amount ranging from about 1% to about 99.9%, preferably from about 50% to about 99.5%, more preferably from about 70% to about 99%, and most preferably from about 80% to 90% by total weight of the topical or cosmetic composition.

The topical or cosmetic composition may contain one or more skin care additives, which are agents that provide benefits to the skin, rather than merely improving the physical or aesthetic characteristics of the topical composition. If present, such skin care actives may range from about 0.01 to 50%, preferably from about 0.05 to 35% by weight of the total composition. Exemplary skin care additives that can be used in the topical or cosmetic compositions of the present invention include, but are not limited to: sunscreen agents, self-tanning agents, anti-aging agents, anti-wrinkle agents, anti-acne agents (e.g., resorcinol, salicylic acid, and the like), enzyme-inhibiting agents, collagen-stimulating agents, agents for the eradication of age spots and keratoses, analgesics, anesthetics, antimicrobials (e.g., antibacterials, anti-yeast agents, antifungal agents, and antiviral agents), antidandruff agents, antidermatitis agents, antipruritic agents, antiemetics, anti-inflammatory agents, antihyperkeratolytic agents, antiperspirants, antipsoriatic agents, antiseborrheic agents, antihistamine agents, skin lightening agents, depigmenting agents, skin soothing/healing agents (e.g., aloe vera extract, allantoin, and the like), corticosteroids, hormones, antioxidants, proteins or peptides, vitamins and derivatives thereof (e.g., vitamin A, vitamin E, vitamin $B_3$, vitamin $B_5$, and the like), exfoliants, retinoids (e.g., retinoic acid and retinol), farnesol, bisabolol, phytantriol, glycerol, urea, guanidine (e.g., amino guanidine), clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, minocycline, hydroquinone, naproxen, ibuprofen, theophylline, cromolyn, albuterol, topical steroids (e.g., hydrocortisone, hydrocortisone 21-acetate, hydrocortisone 17-valerate, and hydrocortisone 17-butyrate), betamethasone valerate, betamethasone diproprionate, benzoyl peroxide, crotamiton, propranolol, promethazine, and mixtures or derivatives thereof. In a preferred, but not necessary embodiment of the present invention, the topical composition comprises one or more skin care actives selected from the group consisting of sunscreen agents, self-tanning agents, anti-aging agents, anti-wrinkle agents, anti-acne agents, antimicrobials, anti-inflammatory agents, skin-lightening agents, antioxidants, proteins or peptides, vitamins and derivatives thereof, exfoliants, and mixtures thereof.

For example, the topical or cosmetic compositions of the present invention may include one or more antioxidants, and more preferably one or more water-soluble extracts of biological materials that exhibit anti-oxidant activities. If present, such antioxidants or water-soluble extracts with antioxidant activities may range from about 0.01 to 45%, preferably from about 0.05 to 20%, more preferably from about 0.1 to 15% by weight of the total composition. Examples of suitable water-soluble extracts that exhibit anti-oxidant activities include, but are not limited to, extracts from: artemia, phytosphingosine, polygonum cuspidatum root, yeast such as *saccharomyces* lysate, *thermos thermophillus* ferment, birch (*Betula alba*), *mimosa tenuiflora* (bark) extract, fruit, clove, rye, malt, corn, spelt, millet, barley, oat, wheat, sesame, cumin, turmeric, green onion, celery, ginseng, ginger, licorice, carrot, bupleurum root, *Ginkgo biloba* (gingko), *Foeniculi Fructus* (fennel), kiwi, berry such as *Morus bombycis* (mulberry), *Gentiana lutea* (gentian), algae such as red algae, *Arctium lappa* (burdock), *Salvia officinalis* (sage), *Lentinus edodes* (shiitake mushroom), *Perilla frutescens* (perilla), *Filipendula Multijuga, Fucus vesiculosis* (bladderwrack, sea weed), peach kernel, *Allium sativum* (garlic), *Poria cocos* (poria), *Humulus lupulus* (hops), *Mutan Cortex* (Moutan Bark), *Pimpinella major, Lactuca sative* (lettuce), *Astragalus membranaceous* (astragalus) and *Rosmarinus officinalis* (rosemary), *Prunus amygdalus* (almond), *Althea officinale* (althea), aloe, *Rosae Fructus* (rose fruit, or *Rosa multiflora*), *Scuttelaria baicalensis* (Huang qin), *Puerariae Radix* (*Pueraria Root*, or *Pueraria lobata*), chamomile such as *Chamomillae Flos* (German chamomile), *Gardenia jasminoides* (zhii zi, *Gardeniae Fructus*), *Sophora flavescens Aiton* (*Sophorae Radix*), chlorella, rice bran, *Paeoniae lacti-*

*flora* (white peony), ziyu (*Sanguisorba officinalis*, burnet), *Moms alba* (sang bai pi, mulberry), *Glycine max* (soybean), *Camellia sinensis* (tea), *Carthami Flos* (safflower), *Aesculus hippocastanum* (horse chestnut), *Melissa officinalis* (lemon balm) and *Coicis Semen* (*Coix lacryma-jobi* var. *ma-yuen*), *Angelica keisukei*, *Arnica montana* (arnica), *Foeniculum officinale* (fennel), *Isodon japonicus Hara* (*Isodonis Herba*), *Daucus Carota* (carrot), *Oryza sativa* (rice), *Crataegus cuneata* (Japanese howthorn), *Acores calamus* (sweet flag), *Crataegus oxycantha* (howthorn), *Juniperus communis*, *Ligusticum wallichii* (Chinese lovage), *Swertiae Herba* (Swertia Herb), *Thymus vulgaris* (garden thyme), *Citrus reticulata* (*Citrus unshiu*), *Capsicum tincture*, *Angelicae sinensis* (angelica), *Aurantii Pericarpium* (bitter orange peel), *Ruscus aculeatus* (butcher's bloom), *Vitis vinifera* (grape), *Tilia japonica* (lime), *Citrus junos* and *Rosa canina* (rose hip), caffeine, *Cinnamomi Cortex* (cinnamon bark) and *Eriobotrya japonica Lindl.* (loquat), *Gambir*, *Echinacea*, *Phellodendri Cortex* (amur cork tree or *Phellodendron amurense*), *Hypericum perforatum* (St. John's wort), *Citrus sinensis* (orange), *Valeriana fauriei Briquet*, *Artemisia capillaris Thunb.*, *Cucumis sativus* (cucumber), *Geranii Herba* (Geranium Herb), *Lithospermum erythrorhizon Sieb.* et *Zucc.*, *Hedera helix*, *Achillea millefolium* (yarrow), *Ziziphus jujuba* (Chinese dates), *Calendula officinalis* (pot marigold), *Houttuynia cordata* (*Houttuyniae Herba*, *Houttuynia Herba*), *Potentilla erecta*, *Petroselinum crispum* (parsley), *Parietaria officinalis*, *Santalum album* (sandalwood), *Prunus persica* (peach), *Centaurea cyanus* (cornflower), *Eucalyptus globulus* (eucalyptus) and *Lavandula angustifolia* (lavender), *Persea americana* (avocado), *Nasturtium officinalis* (watercress), *Symphytum officinale* (comfrey), *Asarum sieboldii* (wild ginger), *Xanthoxyum piperitum* (Japan pepper), *Rehmannia glutinosa* (di huang), *Mentha piperita* (peppermint), *Syzygium aromaticum* (clove), *Tussilago farfara* (coltsfoot) and *Haematoxylum campechianum* (logwood); Oolong tea, *Cinchona succirubra* (peruvian bark), *Betula verrucosa* (birch) and *Glechoma hederacea* (ground ivy), milk and royal jelly, honey, cysteine and derivatives thereof, ascorbic acid and derivatives thereof, BHA, BHT, ferulic acid and derivatives thereof, grapeseed extract, pine bark extract, horseradish extract, hydroquinones, rosmarinic acid, coffee robusta seed, caffeic acid, tocopherol and derivatives thereof, green tea extract, sodium DNA, sodium ribonucleic acid, octyl, propyl and dodecyl gallates, uric acid and thiodiproprionate derivatives.

In a preferred, but not necessary, embodiment of the present invention, one or more of the antioxidant agents as listed hereinabove are co-entrapped into the microspheres together with the particulate components of the present invention. Such co-entrapment can be achieved, for example, by mixing such antioxidant agents together with the particulate components, the hollow microspheres, and the polar organic solvent during the gelling step to form the gelled mixture. Antioxidant agents particularly preferred for co-entrapment with the particulate components of the present invention include, for example, tetrahydrocurcuminoids, ascorbyl tocopheryl maleate (also referred to as 2-CME), grape seed extract, and rosemary extract. A blend or mixture containing all of these particularly preferred antioxidant agents in equal or substantially equal quantities is most preferred for the practice of the present invention. Such co-entrapped antioxidant agents can most effectively scavenge or abate free oxygen radicals generated by the entrapped metal oxide particles, due to their direct contact therewith or spatial proximity thereto.

The antioxidant agents as listed hereinabove can also be used to form an antioxidant coating over the microspheres, which further scavenges or neutralizes free oxygen radicals released therefrom. Further, the antioxidant agents can be provided in a solubilized or dispersed form in the cosmetically or pharmaceutically acceptable carrier of the topical or cosmetic compositions of the present application. Such solubilized or dispersed antioxidant agents function to scavenge or neutralize free oxygen radicals dispersed in the topical or cosmetic compositions, regardless of the source of such free oxygen radicals, thereby further improving the overall stability of the topical or cosmetic compositions of the present invention.

In a particularly preferred embodiment of the present invention, the topical or cosmetic composition is a sunscreen composition comprising microsphere-entrapped zinc oxide particles, or microsphere-entrapped titanium dioxide particles, or both. As mentioned hereinabove, zinc oxide or titanium dioxide particles are known to have photoprotective characteristics and can therefore be used as physical sunscreen agents, but their uses in topical or cosmetic compositions are limited due to their photo-activity, i.e., their tendency to release free oxygen radicals upon exposure to UV light, which may degrade or otherwise interfere with certain organic cosmetic ingredients or skin care actives that are susceptible to oxidative decomposition or degradation. The entrapment of zinc oxide and/or titanium dioxide particles by the microspheres as described in the present invention effectively eliminates or reduces free oxygen radicals from such particles upon UV exposure, but without adversely affecting the sunscreen properties of such particles.

Consequently, the microsphere-entrapped zinc oxide and/or titanium dioxide particles of the present invention can be ready formulated with organic cosmetic ingredients or skin care additives that are known to be susceptible to oxidative decomposition or degradation to form stable sunscreen compositions with significantly improved overall stability and prolonged shelf live. For example, the microsphere-entrapped zinc oxide and/or titanium dioxide particles of the present invention can be formulated with one or more organic dyes susceptible to oxidative decomposition or degradation to form color cosmetic compositions that also have sunscreen properties. For another example, the microsphere-entrapped zinc oxide and/or titanium dioxide particles of the present invention can be formulated with one or more organic sunscreen agents susceptible to oxidative decomposition or degradation, thereby forming sunscreen compositions that are not only characterized by high SPF values (e.g., SPF 30 or more), but also surprisingly and unexpectedly improved overall stability and prolonged shelf life. If present, such organic sunscreen agents may range from about 0.1 to 45% by weight of the total composition.

Exemplary organic sunscreen agents that can be used in combination with the microsphere-entrapped zinc oxide or titanium dioxide particles of the present invention include, but are not limited to UVA and UVB sunscreens, such as benzophenones and derivatives thereof (e.g., benzophenone-3, dioxybenzone, sulisobenzone, octabenzone, hydroxy- and/or methoxy-substituted benzophenones, and benzophenone-sulfonic acids and salts thereof); salicylic acid derivatives (e.g., ethylene glycol salicylate, triethanolamine salicylate, octyl salicylate, homomenthyl salicylate, and phenyl salicylate); urocanic acid and derivatives thereof (e.g., ethyl urocanate); p-aminobenzoic acid (PABA) and derivatives thereof (e.g., ethyl/isobutyl/glyceryl esters thereof and 2-ethylhexyl p-dimethylaminobenzoate, which is also referred to as octyldimethyl PABA); anthranilates and derivatives thereof (e.g., o-amino-benzoates and various esters of amino-benzoic acid); benzalmalonate derivatives; benzimidazole derivatives; imidazolines; bis-benzazolyl derivatives; dibenzoylmethanes and derivatives thereof (e.g., 4-tert-butyl-4'-methoxydibenzoylmethane, which is commonly referred to as "avobenzone," and 4-isopropyl-dibenzoylmethane); benzoazole/benzodiazole/benzotriazoles and derivatives thereof (e.g., 2-(2-hydroxy-5-methylphenyl)benzotriazole and methylene bis-benzotriazolyl tetramethylbutylphenol, which is commonly referred to as "Tinosorb M"); diphenylacrylates and derivatives thereof (e.g., 2-ethylhexyl-2-cyano-3,3-diphenylacrylate, which is commonly referred to as "octocrylene," and ethyl-2-cyano-3,3-diphenylacrylate, which is commonly referred to as "etocrylene"); diesters or polyesters containing diphenylmethylene or 9H-fluorene substitutional groups; 2-phenyl-benzimidazole-5-sulphonic acid (PBSA); 4,4-diarylbutadienes; cinnamates and derivatives thereof (e.g., 2-ethylhexyl-p-methoxycinnamate, octyl-p-methoxycinnamate, umbelliferone, methylumbelliferone, methylaceto-umbelliferone, esculetin, methylesculetin, and daphnetin); camphors and derivatives thereof (e.g., 3-benzylidenecamphor, 4-methylbenzylidenecamphor, polyacrylamidomethyl benzylidenecamphor, benzylidene camphor sulfonic acid, and terephthalylidene dicamphor sulfonic acid, which is commonly referred to as "Encamsule"); triazines and derivatives thereof (e.g., 2,4-bis-{[4-(2-ethyl-hexyloxy)-2-hydroxy]-phenyl}-6-(4-methoxyphenyl)-1,3,5-triazine, which is commonly referred to as "Tinosorb S"); naphthalates and derivatives thereof (e.g., diethylhexyl-2,6-naphthalate); naphtholsulfonates and derivatives thereof (e.g., sodium salts of 2-naphthol-3,6-disulfonic and 2-naphthol-6,8-disulfonic acids); dibenzalacetone and benzalacetonephenone; diphenylbutadienes and derivatives thereof; dihydroxynaphthoic acid and salts thereof; o- and p-hydroxybiphenyldisulfonates; coumarin derivatives (e.g., 7-hydroxy, 7-methyl, and 3-phenyl derivatives thereof); azoles/diazoles/triazoles and derivatives thereof (e.g., 2-acetyl-3-bromoindazole, phenyl benzoxazole, methyl naphthoxazole, and various aryl benzotriazoles); quinine and derivatives thereof (e.g., bisulfate, sulfate, chloride, oleate, and tannate salts thereof); quinoline and derivatives thereof (e.g., 2-phenylquinoline and 8-hydroxyquinoline salts); tannic acid and derivatives thereof (e.g., hexaethylether derivatives thereof); hydroquinone and derivatives thereof; uric acid and derivatives thereof; vilouric acid and derivatives thereof, and mixtures or combinations thereof. Salts and otherwise neutralized forms of certain acidic sunscreens from the list hereinabove are also useful herein. These organic sunscreen agents may be used alone or in combination of two or more. In addition, other known animal or vegetable extracts having UV light-absorbing ability may properly be used alone or in combination.

Organic sunscreen agents that are particularly useful for the practice of the present invention are: 4,4'-t-butyl methoxydibenzoylmethane, 2-ethylhexyl-2-cyano-3,3-diphenylacrylate, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethyl-hexyloxy)-2-hydroxy]-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)] aminobenzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof. Preferably, 4,4'-t-butyl methoxydibenzoylmethane is provided in the sunscreen compositions of the present invention, either with microsphere-entrapped titanium dioxide or microsphere-entrapped zinc oxide, or both. More preferably, the sunscreen compositions of the present invention further include a second organic sunscreen agent selected from the lists provided hereinabove.

The above-described organic sunscreen agents may be solubilized or freely dispersed in the cosmetically or pharmaceutically acceptable carrier of the topical or cosmetic compositions of the present application. Alternatively, the organic sunscreen agents can be provided in a protected form, i.e., encapsulated in protective structures. For example, the organic sunscreen agents can be encapsulated or entrapped into additional microspheres similar to those described hereinabove, i.e., with collapsed polymeric shells. In this manner, the organic sunscreen agents are further protected from free oxygen radicals or other radicals in the surrounding environment that may destabilize or degrade such organic sunscreen agents.

The cosmetically acceptable carrier may also contain one or more oils, which may be silicone, organic, or mixtures thereof. If present, such oils may range from about 0.1 to 99% by weight of the total composition and include volatile or non-volatile silicones such as cyclomethicone; methyl trimethicone; octamethyltrisiloxane; decamethyltetrasiloxane; dodecamethylpentasiloxane; dimethicone; phenyl trimethicone trimethylsiloxyphenyl dimethicone; phenyl dimethicone; cetyl dimethicone; dimethicone copolyol, cetyl dimethicone copolyol; glycerolated silicones such as lauryl PEG-9 polydimethylsiloxyethyl dimethicone; or mixtures thereof. Suitable esters include mono-, di-, or triesters of C4-30 fatty acids and mono-, di-, or polyhydric C1-20 alcohols, such as fatty acid (e.g., stearyl, behenyl, and isostearyl) esters of glycerin, or fatty acid esters of alpha hydroxyl acids such as citric, malic, or lactic acids and the like. Suitable hydrocarbons include monomeric or polymeric olefins or alpha olefins, such as polyisobutene, polydecene, polybutene, or hydrogenated derivatives thereof.

The cosmetically acceptable carrier may also comprise one or more humectants. If present, they may range from about 0.1 to 20% by weight of the total composition and include C1-4 alkylene glycols such as butylene, propylene, ethylene glycol, glycerin and the like.

The cosmetically acceptable carrier may also contain one or more waxes preferably having a melting point ranging from about 30 to 150° C. If present, such waxes may range from about 0.1 to 45% by weight of the total composition and include animal, vegetable, mineral, or silicone waxes. Examples include alkyl dimethicones stearyl dimethicone, candelilla, polyethylene, ozokerite, beeswax, and the like.

The cosmetically acceptable carrier may also comprise one or more organosiloxane elastomers, either emulsifying or non-emulsifying. If present, such elastomers may range from about 0.1 to 30% by weight of the total composition. Examples of suitable elastomers include dimethicone/vinyl dimethicone crosspolymer; dimethicone/dimethicone PEG/PPG 10/15 crosspolymer; and the like.

The cosmetically acceptable carrier may also include one or more pigments or powders or mixtures thereof. If present, the suggested ranges of such pigments or powders are from about 0.1 to 85% by weight of the total composition. The particle sizes of such pigments or powders may range from about 0.05 to 200 microns but are preferably about 50-100 microns. Examples of pigments include organic pigments such as D&C or FD&C colors or Lakes thereof including blues, browns, reds, etc; or inorganic iron oxides such as brown, yellow, green, red, iron oxides. Suitable powders include titanium dioxide, nylon, PMMA, boron nitride, mica, and the like.

The cosmetically acceptable carrier may also comprise one or more nonionic surfactants, particularly if the topical or cosmetic composition of the present invention is provided in the emulsion form. If present, such surfactants may range from about 0.1 to 20% by weight of the total composition. Suitable surfactants include ethoxylated fatty C6-30 alcohols such as steareth, beheneth, ceteth where the number following each of the surfactants refers to the number of repeating ethylene oxide groups which may range from 2 to 250, e.g. steareth-2, beheth-30 and so on.

The present invention can be further illustrated in the following non-limiting examples.

Example I

Expancel 551 DE 20 d 60 (DE 20 stands for average particle size of 20 microns)—about 800 g is placed into a mixing chamber. Acetone in an amount of about 4,000 mL is added under 20 RPM. A gel is formed and about 343 g of ultra fine titanium dioxide (D 50 2 microns) are added to the gel. The combination of titanium dioxide and the gel is mixed until homogeneous. The acetone is removed by heating the combination in a vacuum chamber. The titanium dioxide particles are entrapped in the microspheres and the outer layer of the microsphere is over-coated with about 14 percent by weight of a Dow Corning 1107 silicone polymer. The final particle size of the $TiO_2$-entrapping microspheres is measured using a Malvern Particle Size Analyzer, available from Malvern Instrument Scirocco 2000 at Worcestershire, UK and the result is between 5 to 8 microns.

Example II

Following the process outlined in Example I using Expancel 461 DE 40 d60 the same result is obtained, the final particle size of the $TiO_2$-entrapping microspheres is between 5 to 8 microns.

Example III

Example I was repeated with irregular solid particles of Dow Chemical Saran F 310 (Polyvinylidene Chloride). This experiment was performed in order to prove ability of particles to be dispersed in a gelled polymer, regardless it's original shape or composition.

Example IV

Expancel 551 DE 20 d 60 of about 300 g is placed into a mixing chamber. Acetone in an amount of about 2,550 mL is added under 20 RPM. A gel is formed and about 463 g of ultra fine zinc dioxide (D 50 2 microns) are added to the gel. The combination of zinc dioxide and the gel is mixed until homogeneous. The acetone is removed by heating the combination in a vacuum chamber. The zinc oxide particles are entrapped in the microspheres and the outer layer of the microsphere is over-coated with about 10 percent by weight of a Dow Corning 7-4404 cosmetic fluid. The final particle size of the ZnO-entrapping microspheres is measured using a Malvern Particle Size Analyzer, available from Malvern Instrument at Worcestershire, UK and the result is between 5 to 8 microns.

Example V

A comparative test was conducted to show photodegradation of an organic dye, namely, D&C Red No. 28 (or Red 28), under UV exposure and in the presence of various $TiO_2$ particles, either un-encapsulated (i.e., naked) or entrapped with or without antioxidants in microspheres of the present invention as described hereinabove.

Specifically, an ethanol solution containing 0.013 wt % of Red 28 was provided as a control sample. Several comparative samples were then prepared, which respectively contained: (1) 0.011 wt % of Red 28 and 0.02 wt % of un-encapsulated or naked $TiO_2$ particles with an average particle size of about 20-50 nm as dispersed in ethanol; (2) 0.011 wt % of Red 28 and 0.04 wt % of $TiO_2$-entrapping microspheres with co-entrapped antioxidants (which contain titanium dioxide, aluminum hydroxide/stearic acid, polyvinylidene chloride/acrylonitrile copolymer, methicone, and tetrahydrocurcuminoids) as dispersed in ethanol; and (3) 0.011 wt % of Red 28 and 0.04 wt % of $TiO_2$-entrapping microspheres without any antioxidants (which contain titanium dioxide, aluminum hydroxide/stearic acid, polyvinylidene chloride/acrylonitrile copolymer, and methicone) as dispersed in ethanol.

Light transmission at a wavelength of about 400-700 nm by the control sample and the comparative samples before any UV exposure were measured by a Spectroflash SF600 Plus-CT colorimeter commercially available from DataColor at Lawrenceville, N.J. The control sample and the comparative samples were then exposed to UV light of about 275 J. After the UV exposure, light transmission at 400-700 nm by the control sample and comparative samples were measured again and compared with the light transmission values before the UV exposure, and DE color shifts of about 7.34 for the control sample, 9.32 for the $TiO_2$-entrapping microspheres without any antioxidants, 3.89 for the $TiO_2$-entrapping microspheres with co-entrapped antioxidants, and 82.77 for un-encapsulated or naked $TiO_2$ particles were calculated based on such measurements.

Figure 3:
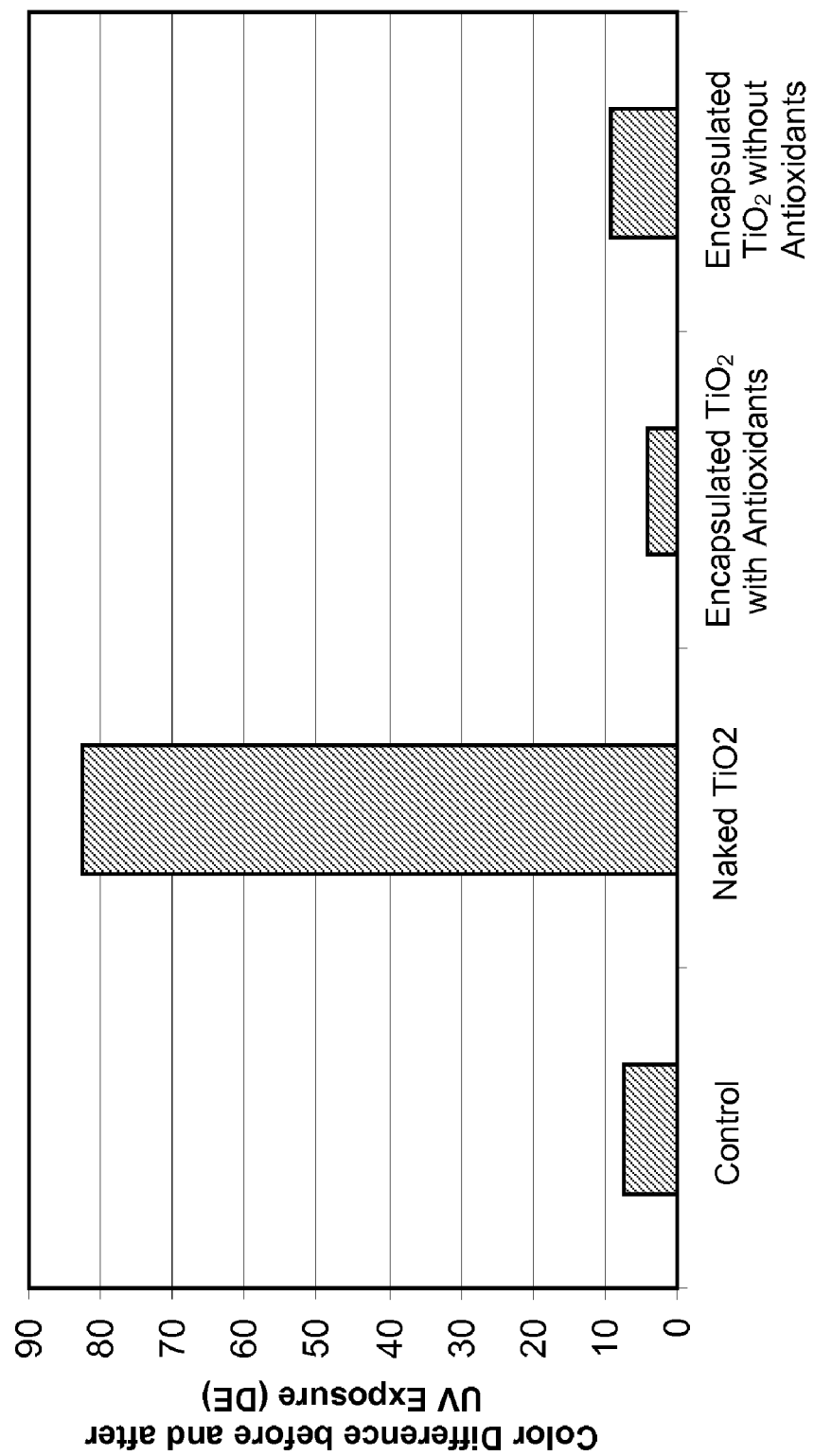
FIG. 3 is a graph showing percentage color changes (%) of an organic dye (Red 28) after 22 hours of exposure to ultraviolet (UV) light, while the organic dye was provided either alone as a control sample or in combination with various types of $TiO_2$ particles, including un-encapsulated (or naked) $TiO_2$ particles and microsphere-entrapped $TiO_2$ particles either with or without antioxidants, according to alternative embodiments of the present invention.

FIG. 3 is a graph showing the percentage color changes of various samples described hereinabove, which include (from left to right): the control sample, the comparative sample (1), the comparative sample (2) and the comparative sample (3). It is clear from FIG. 3 that when combined with un-encapsulated or naked $TiO_2$ particles, a majority of the organic dye Red 28 was degraded upon UV exposure, while entrapment of the $TiO_2$ particles into the microspheres of the present invention, either with or without antioxidants, effectively reduced the degradation of such organic dye to a level that was either comparable with or lower than the control sample.

Example VI

A comparative test was conducted to show UV absorbance spectra of un-encapsulated (or naked) $TiO_2$ particles and microsphere-entrapped $TiO_2$ particles of the present invention.

The following two formulas (I and II), one of which contained naked $TiO_2$ particles and the other of which contained microsphere-entrapped $TiO_2$ particles of the present invention, were prepared:

| Components | wt % in Formula I (with Naked $TiO_2$) | wt % in Formula II (with Entrapped $TiO_2$) |
|---|---|---|
| Deionized water | 35.07 | 30.59 |
| Naked TiO (titanium dioxide/aluminum hydroxide/stearic acid in trioctyldodecyl citrate) | 17.40 | — |

-continued

| Components | wt % in Formula I (with Naked TiO$_2$) | wt % in Formula II (with Entrapped TiO$_2$) |
|---|---|---|
| Microsphere-entrapped TiO$_2$ (titanium dioxide, aluminum hydroxide/stearic acid, polyvinylidene chloride/acrylonitrile copolymer, and methicone) | — | 13.00 |
| Butylene glycol | 8.00 | 8.00 |
| Cyclopentasiloxane | 7.00 | 6.00 |
| Isopropyl titanium triisostearate/C$_{12}$-C$_{15}$ alkyl benzoate/polyglyceryl-6 polyricinoleate/zinc oxide/caprylyl methicone | 6.00 | 6.00 |
| Tricaprylin | 3.42 | 3.00 |
| Trioctyldodecyl citrate | 2.75 | 11.52 |
| Steareth-2 | 2.42 | 2.42 |
| Tricaprylyl citrate | 2.00 | 2.50 |
| Silica | 2.00 | 2.00 |
| Dipentaerythrityl tri-polyhydroxystearate | 2.00 | 2.00 |
| Stearyl dimethicone | 1.93 | 1.93 |
| Lecithin | 1.00 | 1.00 |
| Calcium sulfate | 1.00 | 1.00 |
| Titanium dioxide/methicone | 1.00 | 1.00 |
| Barium sulfate | 1.00 | 1.00 |
| Sorbitan tristearate | 0.77 | 0.77 |
| Magnesium aluminum silicate | 0.60 | 0.60 |
| Silver borosilicate | 0.50 | 0.50 |
| Dimethicone | 0.50 | 0.50 |
| PEG-40 stearate | 0.41 | 0.41 |
| Ceteth-2 | 0.41 | 0.41 |
| PEG/PPG-18/18 dimethicone | 0.40 | 1.50 |
| Xanthan gum | 0.40 | 0.40 |
| Iron oxide yellow | 0.40 | 0.33 |
| Phosphoric acid | 0.30 | 0.30 |
| Tocopheryl acetate (Vitamin E) | 0.25 | 0.25 |
| Magnesium ascorbyl phosphate | 0.25 | 0.25 |
| Steareth-20 | 0.22 | 0.22 |
| Disodium EDTA | 0.20 | 0.20 |
| Pantethine | 0.10 | 0.10 |
| Sodium stearate | 0.10 | 0.10 |
| BHT | 0.10 | 0.10 |
| Bisabolol | 0.05 | 0.05 |
| Iron oxide red | 0.02 | 0.02 |
| Iron oxide black | 0.02 | 0.02 |

Figure 4:
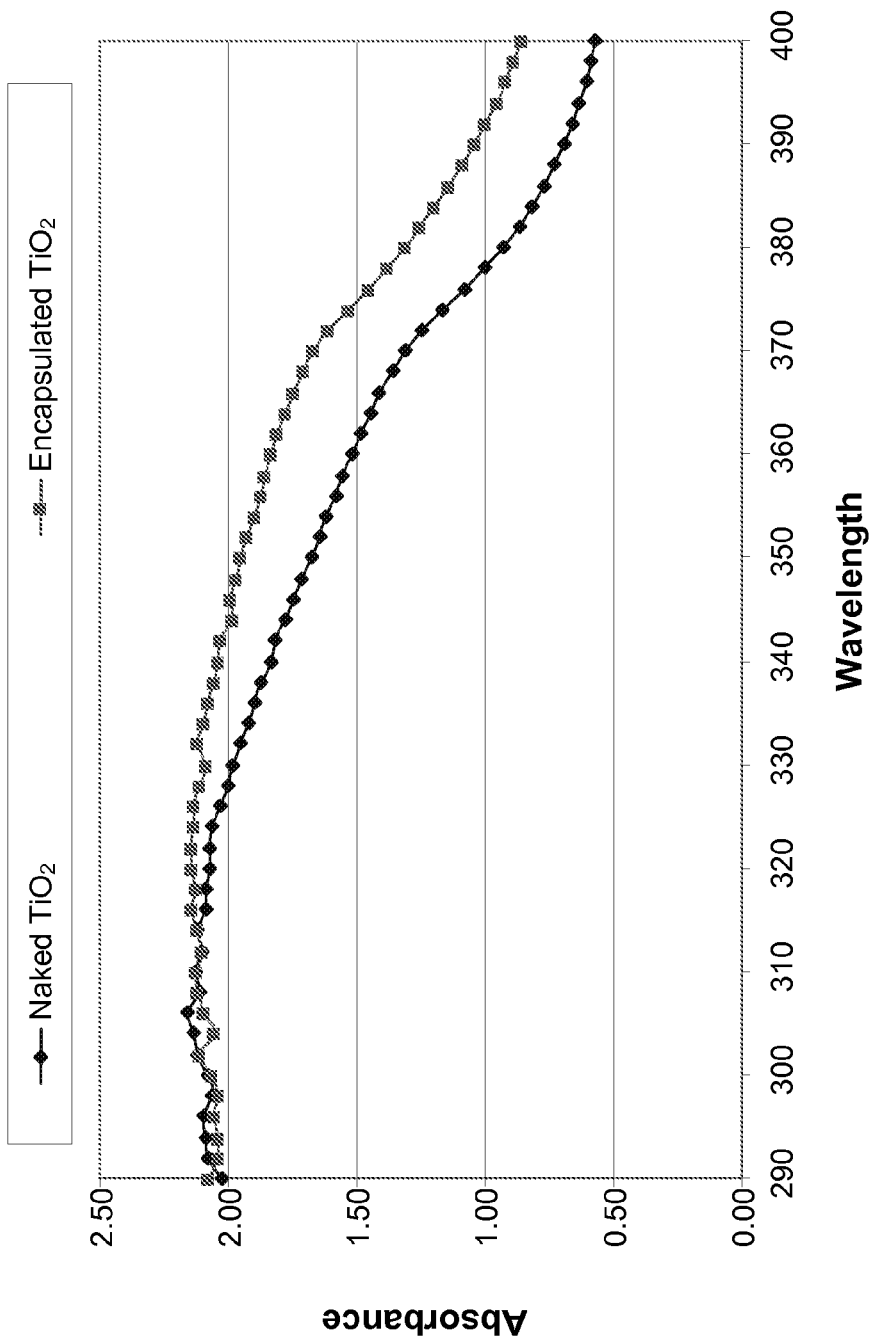
FIG. 4 shows UV absorption spectra of sunscreen compositions containing either un-encapsulated (or naked) $TiO_2$ particles or microsphere-entrapped $TiO_2$ particles of the present invention after exposure to UV light.

The above-described two formulas were exposed to UV light of about 225 J emitted by a Thermo Oriel-Solar simulator manufactured by Newport Corporation at Stanford, Conn. The photo-absorbance of the two formulas during the UV exposure was measured by a Radiometer/Photometer manufactured by International Light Technologies at Peabody, Mass. and plotted in FIG. 4. It is clear from FIG. 4 that in comparison with un-encapsulated or naked TiO$_2$ particles, the microsphere-entrapped TiO$_2$ particles demonstrated comparable absorbance at the UVB range (at wavelength about 280-315 nm) and significantly higher absorbance at the UVA range (at wavelength about 315 nm-400 nm).

Example VII

A comparative test was conducted to show photostability of 4,4'-t-butyl methoxydibenzoylmethane (Avobenzone) in the presence of un-encapsulated or naked TiO$_2$ particles and the microsphere-entrapped TiO$_2$ particles of the present invention.

The following two formulas (III and IV), one of which contained naked TiO$_2$ particles and the other of which contained microsphere-entrapped TiO$_2$ particles of the present invention, were prepared:

| Components | wt % in Formula III (with Naked TiO$_2$) | wt % in Formula IV (with Entrapped TiO$_2$) |
|---|---|---|
| Deionized water | 51.50 | 44.90 |
| Coated TiO$_2$ (titanium dioxide/aluminum hydroxide/stearic acid in trioctyldodecyl citrate) | 17.40 | — |
| Microsphere-entrapped TiO$_2$ (polyvinylidene chloride/acrylonitrile copolymer, titanium dioxide, stearic acid, aluminum hydroxide, and methicone) | — | 13.00 |
| Neopentyl glycol diheptanoate | 9.50 | 9.50 |
| Butylene glycol | 4.00 | 4.00 |
| Ceterayl olivate/sorbitan olivate | 4.00 | 4.00 |
| Kukui nut oil | 3.00 | 3.00 |
| Avobenzone | 3.00 | 3.00 |
| Lauryl PEG-9 polydimethylsiloxyethyl dimethicone | 3.00 | 3.00 |
| Hydrogenated olive oil/olive oil/olive oil unsaponifiables | 2.00 | 2.00 |
| Dimethicone | 1.00 | 1.00 |
| Cetyl alcohol | 0.75 | 0.75 |
| Silver borosilicate | 0.50 | 0.50 |
| Xanthan gum | 0.25 | 0.25 |
| Disodium EDTA | 0.10 | 0.10 |
| Trioctyldodecyl citrate | — | 11.00 |

Figure 5A:
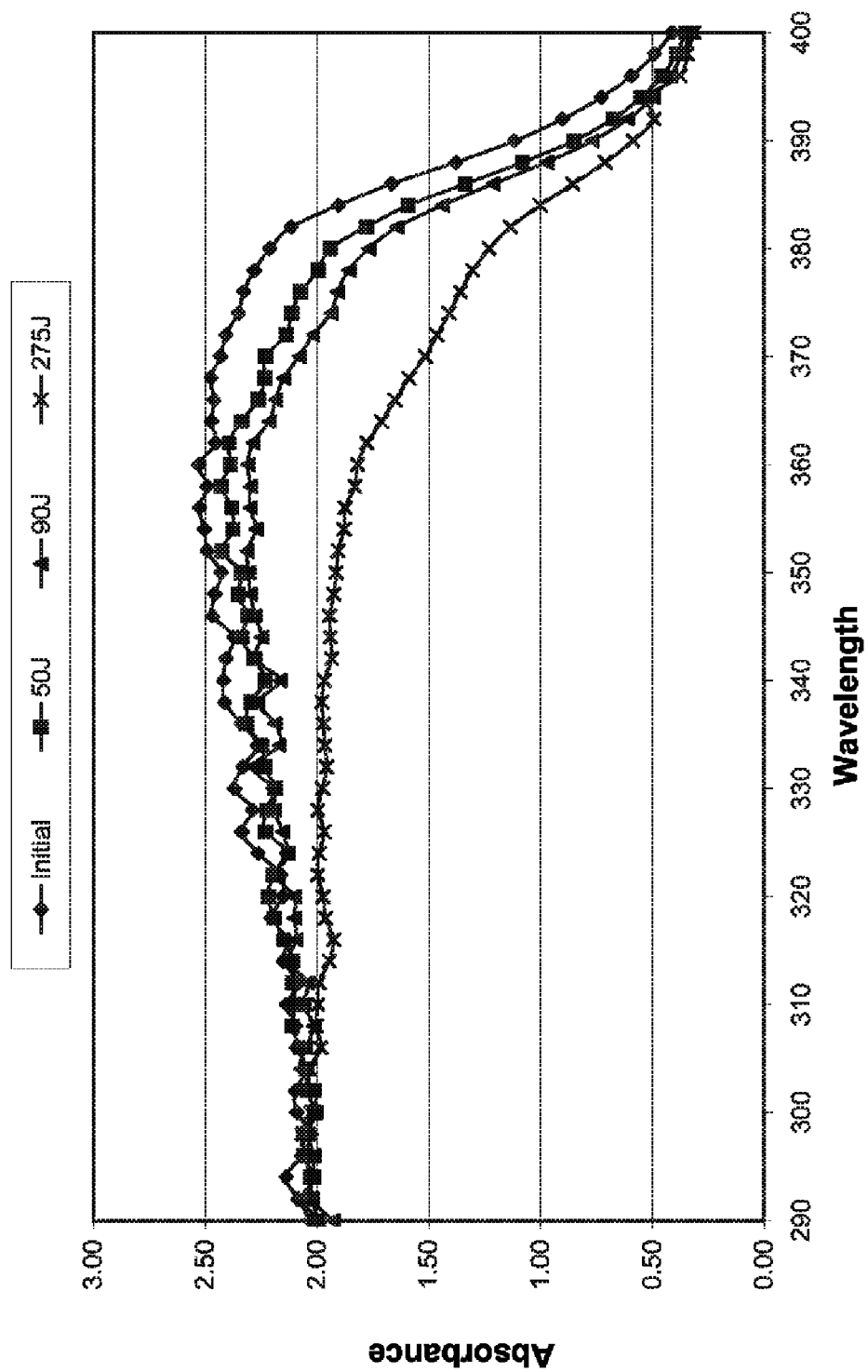
FIG. 5A shows photo-absorbance curves of a sunscreen composition containing un-encapsulated (or naked) $TiO_2$ particles and avobenzone, after exposure to UV light at various intensities.
Figure 5B:
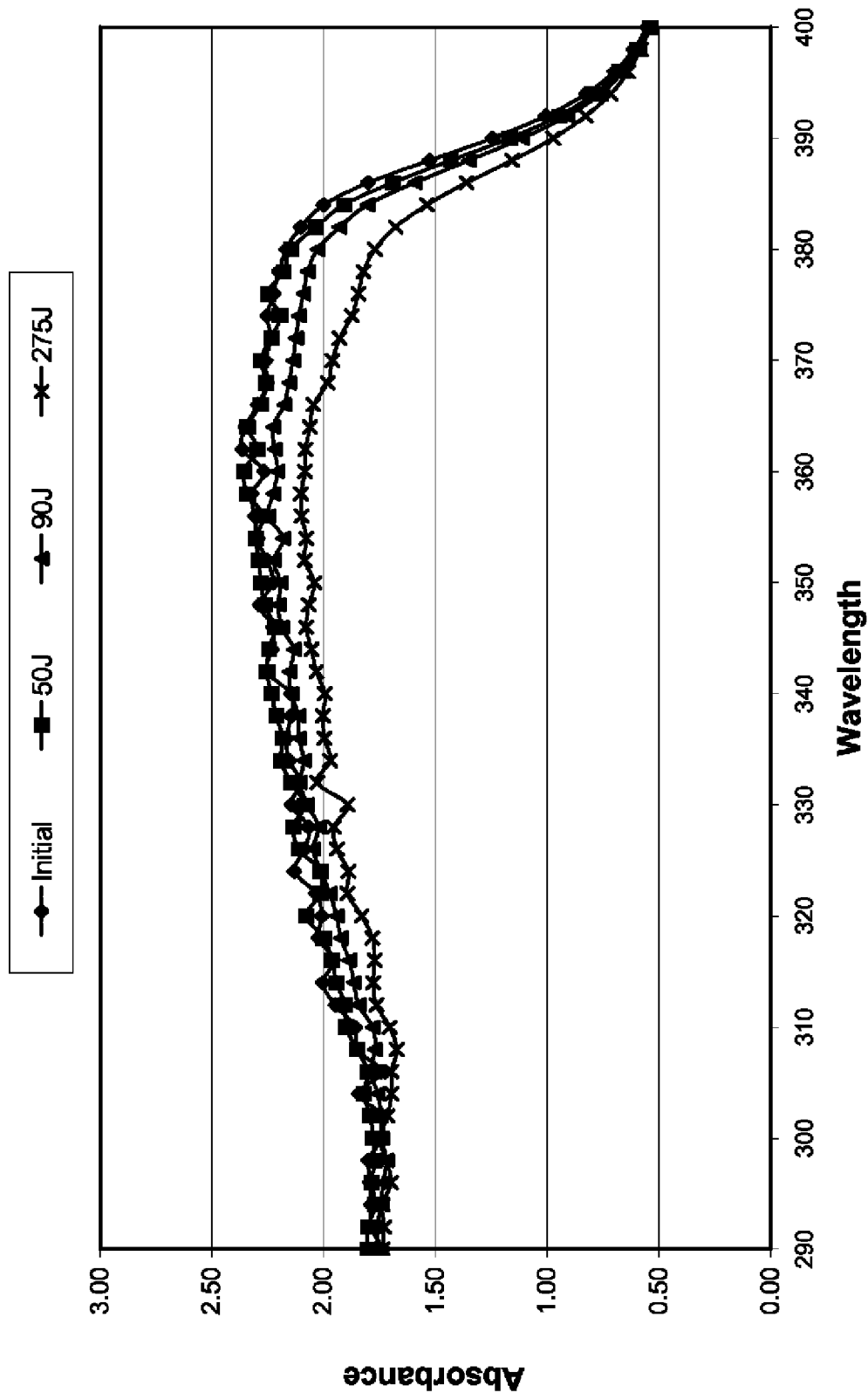
FIG. 5B shows photo-absorbance curves of a sunscreen composition containing microsphere-entrapped $TiO_2$ particles of the present invention and avobenzone, after exposure to UV light at various intensities.

The above-described two formulas were exposed to UV light at various intensities, namely, 50 J, 90 J, and 275 J, emitted by a Thermo Oriel-Solar simulator manufactured by Newport Corporation at Stratford, Conn. The photo-absorbance of these two formulas before and after the UV exposure was measured by a Radiometer/Photometer manufactured by International Light Technologies at Peabody, Mass. 01960. The initial photo-absorbance of such formulas before the UV exposure was recorded as the baseline values. FIG. 5A shows the photo-absorbance curves of Formula III at the initial state (i.e., before the UV exposure) and after exposure to UV light at 50 J, 90 J, and 275 J. FIG. 5B shows the photo-absorbance curves of Formula IV at the initial state (i.e., before the UV exposure) and after exposure to UV light at 50 J, 90 J, and 275 J.

It is clear that when combined with naked TiO$_2$ particles, avobenzone was significantly less photo-stable than when combined with the microsphere-entrapped TiO$_2$ particles of the present invention, which is demonstrated by the significantly greater reduction in the photo-absorbance of Formal III in comparison with that of Formula IV after exposure to UV light at a higher intensity (e.g., 275 J), as shown in FIGS. 5A and 5B.

Example VIII

Following are several exemplary topical or cosmetic sunscreen formulas containing either microsphere-entrapped TiO$_2$ particles or microsphere-entrapped ZnO particles of the present invention.

Sunscreen Formula 1

This face lotion is an oil-in-water emulsion containing the microsphere-entrapped $TiO_2$ particles of the present invention (without any co-entrapped antioxidant) in combination with several organic sunscreen agents including Avobenzone:

| Components | wt % |
| --- | --- |
| Deionized water | 35.08 |
| Disodium EDTA | 0.10 |
| Sodium dehydroacetate | 0.10 |
| Acetyl glucosamine | 0.05 |
| Caffeine | 0.20 |
| Butylene glycol | 2.00 |
| Dehydroxanthan gum | 0.25 |
| Avobenzone | 3.00 |
| Ethylhexyl salicylate | 5.00 |
| Benzophenone-3 | 5.00 |
| Polyester-8 | 3.00 |
| Butyloctyl salicylate | 4.00 |
| $C_{30}$-$C_{38}$ olefin/isopropyl maleate/MA copolymer | 0.75 |
| VP/eicosene copolymer | 0.75 |
| Potassium cetyl phosphate | 1.00 |
| PEG-100 stearate | 2.25 |
| Glyceryl stearate | 1.50 |
| Cetyl alcohol | 0.75 |
| Stearic acid | 0.75 |
| Homosalate | 5.00 |
| Kukui nut oil | 3.00 |
| Dipentaerythrityl tri-polyhydroxystearate | 1.50 |
| Turmeric root extract | 0.01 |
| Microsphere-entrapped $TiO_2$ (titanium dioxide, aluminum hydroxide/stearic acid, polyvinylidene chloride/acrylonitrile copolymer, and methicone) | 6.00 |
| Mica | 5.00 |
| Lauryl PEG-9 polydimethylsiloxyethyl dimethicone | 2.00 |
| Methyl trimethicone | 5.00 |
| Caprylyl methicone | 1.50 |
| Ethylhexyl glycerin | 0.50 |
| Phenoxyethanol/caprylyl glycol/sorbic acid | 0.85 |
| Ammonium acrylodimethyltaurate/VP copolymer | 0.20 |
| Mulberry root extract/scutellaria baicalensis extract/grape extract | 0.10 |
| Yeast extract | 0.01 |
| Whey protein | 0.01 |
| Fragrance | 0.20 |

Sunscreen Formula 2

This face lotion is an oil-in-water emulsion containing the microsphere-entrapped ZnO particles of the present invention (without any co-entrapped antioxidant) in combination with several organic sunscreen agents including Avobenzone:

| Components | wt % |
| --- | --- |
| Deionized water | 30.86 |
| Disodium EDTA | 0.10 |
| Dipentaerythrityl tri-polyhydroxystearate | 2.00 |
| Butylene glycol | 4.00 |
| Xanthan gum | 0.20 |
| Acrylic acid/VP crosspolymer | 0.25 |
| Avobenzone | 3.00 |
| Ethylhexyl salicylate | 5.00 |
| Mica | 5.00 |
| Polyester-8 | 3.00 |
| Butyloctyl salicylate | 3.50 |
| Neopentyl glycol diheptanoate | 2.50 |
| $C_{30}$-$C_{38}$ olefin/isopropyl maleate/MA copolymer | 0.80 |
| Octocrylene | 2.79 |
| Cetyl alcohol | 0.75 |
| VP/eicosene copolymer | 0.50 |
| Potassium cetyl phosphate | 1.00 |
| PEG-100 stearate | 2.25 |
| Glyceryl stearate | 1.50 |
| Homosalate | 5.00 |
| Kukui nut oil | 6.00 |
| Benzophenone-3 | 5.00 |
| Styrene/acrylates copolymer//PEG-8 laurate//water | 1.00 |
| Microsphere-entrapped ZnO (zinc oxide, isopropyl titanium, triisostearate, polyvinylidene chloride/acrylonitrile copolymer, and methicone) | 6.00 |
| Lauryl PEG-9 polydimethylsiloxyethyl dimethicone | 2.00 |
| Methyl trimethicone | 3.00 |
| Caprylyl methicone | 1.50 |
| Ethylhexyl glycerin | 0.50 |
| Phenoxyethanol/caprylyl glycol/sorbic acid | 0.85 |
| Tromethamine | 0.15 |

Sunscreen Formula 3

This face lotion is a water-in-silicone emulsion containing the microsphere-entrapped $TiO_2$ particles of the present invention (without any co-entrapped antioxidant):

| Components | wt % |
| --- | --- |
| Deionized water | 41.68 |
| Dipentaerythrityl tri-polyhydroxystearate | 2.00 |
| Butylene glycol | 6.00 |
| Xanthan gum | 0.25 |
| Glycerin | 2.00 |
| Phenoxyethanol/caprylyl glycol | 0.85 |
| Phenoxyethanol | 0.20 |
| Magnesium sulfate | 1.00 |
| Cetyl PEG/PPG-10/1 dimethicone | 1.00 |
| Titanium dioxide/methicone | 4.35 |
| Microsphere-entrapped $TiO_2$ (titanium dioxide, polyvinylidene chloride/acrylonitrile copolymer/trimethylated silica) | 8.70 |
| Dimethicone//dimethicone PEG-10/15 crosspolymer | 2.00 |
| Lauryl PEG-9 polydimethylsiloxyethyl dimethicone | 1.00 |
| Dimethicone/vinyl dimethicone crosspolymer//methyl trimethicone | 1.50 |
| Pantethine | 0.50 |
| Tocopheryl acetate | 0.20 |
| Neopentyl glycol diethylhexanoate | 7.50 |
| Polydiethylsiloxane | 3.00 |
| Methyl trimethicone | 16.27 |

Sunscreen Formula 4

This face lotion is an oil-in-water emulsion containing the microsphere-entrapped $TiO_2$ particles of the present invention with co-entrapped antioxidants and in combination with Avobenzone:

| Components | wt % |
| --- | --- |
| Deionized water | 39.15 |
| Disodium EDTA | 0.10 |
| Caffeine | 0.20 |
| Butylene glycol | 3.00 |
| Dehydroxanthan gum | 0.30 |
| VP/eicosene copolymer | 0.75 |
| Potassium cetyl phosphate | 1.00 |
| PEG-100 stearate | 2.25 |
| Glyceryl stearate | 1.50 |

-continued

| Components | wt % |
|---|---|
| Cetyl alcohol | 0.75 |
| Stearic acid | 0.75 |
| *Kukui* nut oil | 6.00 |
| Dipentaerythrityl tri-polyhydroxystearate | 1.50 |
| Butyloctyl salicylate | 4.00 |
| Neopentyl glycol diheptanoate | 7.00 |
| $C_{30}$-$C_{38}$ olefin/isopropyl maleate/MA copolymer | 0.75 |
| Dioctyl succinate | 10.00 |
| Avobenzone | 3.00 |
| Polyester-8 | 3.00 |
| Microsphere-entrapped $TiO_2$ with antioxidants (titanium dioxide, polyvinylidene chloride/acrylonitrile copolymer/trimethylated silica, and tetrahydrocurcuminoids) | 6.00 |
| Lauryl PEG-9 polydimethylsiloxyethyl dimethicone | 3.00 |
| Methyl trimethicone | 5.00 |
| Ethylhexyl glycerin | 0.30 |
| Phenoxyethanol/caprylyl glycol | 0.50 |
| Ammonium acrylodimethyltaurate/VP copolymer | 0.20 |

Sunscreen Formula 5

This face lotion is an oil-in-water emulsion containing the microsphere-entrapped $TiO_2$ particles of the present invention (without any co-entrapped antioxidant) in combination with several organic sunscreen agents (without Avobenzone):

| Components | wt % |
|---|---|
| Deionized water | 38.08 |
| Disodium EDTA | 0.10 |
| Sodium dehydroacetate | 0.10 |
| Acetyl glucosamine | 0.05 |
| Caffeine | 0.20 |
| Butylene glycol | 2.00 |
| Dehydroxanthan gum | 0.25 |
| Ethylhexyl salicylate | 5.00 |
| Benzophenone-3 | 5.00 |
| Polyester-8 | 3.00 |
| Butyloctyl salicylate | 4.00 |
| Neopentyl glycol diheptanoate | 3.50 |
| $C_{30}$-$C_{38}$ olefin/isopropyl maleate/MA copolymer | 0.75 |
| VP/eicosene copolymer | 0.75 |
| Potassium cetyl phosphate | 1.00 |
| PEG-100 stearate | 2.25 |
| Glyceryl stearate | 1.50 |
| Cetyl alcohol | 0.75 |
| Stearic acid | 0.75 |
| Homosalate | 5.00 |
| *Kukui* nut oil | 3.00 |
| Dipentaerythrityl tri-polyhydroxystearate | 1.50 |
| Turmeric root extract | 0.01 |
| Microsphere-entrapped $TiO_2$ (titanium dioxide/aluminum hydroxide/stearic acid, polyvinylidene chloride/acrylonitrile copolymer, and methicone) | 6.00 |
| Mica | 5.00 |
| Lauryl PEG-9 polydimethylsiloxyethyl dimethicone | 2.00 |
| Methyl trimethicone | 5.00 |
| Caprylyl methicone | 1.50 |
| Ethylhexyl glycerin | 0.50 |
| Phenoxyethanol/caprylyl glycol/sorbic acid | 0.85 |
| Ammonium acrylodimethyltaurate/VP copolymer | 0.20 |
| Mulberry root extract/*scutellaria baicalensis* extract/grape extract | 0.10 |
| Yeast extract | 0.01 |
| Whey protein | 0.01 |
| Fragrance | 0.20 |

Sunscreen Formula 6

This face lotion is an oil-in-water emulsion containing the microsphere-entrapped ZnO particles of the present invention (without any co-entrapped antioxidant) in combination with several organic sunscreen agents including Avobenzone:

| Components | wt % |
|---|---|
| Deionized water | 33.82 |
| Disodium EDTA | 0.10 |
| Dipentaerythrityl tri-polyhydroxystearate | 2.00 |
| Caprylyl glycol | 0.30 |
| Butylene glycol | 4.00 |
| Xanthan gum | 0.30 |
| Avobenzone | 3.00 |
| Ethylhexyl salicylate | 5.00 |
| Mica | 5.00 |
| Octocrylene | 2.79 |
| Butyloctyl salicylate | 5.00 |
| Neopentyl glycol diheptanoate | 1.50 |
| $C_{30}$-$C_{38}$ olefin/isopropyl maleate/MA copolymer | 0.80 |
| VP/eicosene copolymer | 0.50 |
| Potassium cetyl phosphate | 1.00 |
| PEG-100 stearate | 2.25 |
| Glyceryl stearate | 1.50 |
| Cetyl alcohol | 0.75 |
| Homosalate | 5.00 |
| *Kukui* nut oil | 5.00 |
| Silica | 2.00 |
| Styrene/acrylates copolymer//PEG-8 laurate//water | 1.00 |
| Lauryl PEG-9 polydimethylsiloxyethyl dimethicone | 2.00 |
| Methyl trimethicone | 5.00 |
| Dimethicone | 1.50 |
| Microsphere-entrapped ZnO (zinc oxide/diphenyl capryl methicone, polyvinylidene chloride/acrylonitrile copolymer/trimethylated silica) | 7.44 |
| Ethylhexyl glycerin | 0.50 |
| Phenoxyethanol/caprylyl glycol | 0.85 |
| Caprylic/capric triglyceride/*laminaria ochroleuca* extract | 0.10 |

Sunscreen Formula 7

This face lotion is a water-in-silicone emulsion containing the microsphere-entrapped $TiO_2$ particles of the present invention (without any co-entrapped antioxidant):

| Components | wt % |
|---|---|
| Deionized water | 39.67 |
| Dipentaerythrityl tri-polyhydroxystearate | 2.00 |
| Butylene glycol | 6.00 |
| Xanthan gum | 0.25 |
| Glycerin | 2.00 |
| Phenoxyethanol/caprylyl glycol | 0.85 |
| Phenoxyethanol | 0.20 |
| Magnesium sulfate | 1.00 |
| Cetyl PEG/PPG-10/1 dimethicone | 1.00 |
| Microsphere-entrapped $TiO_2$ (titanium dioxide/polyvinylidene chloride/acrylonitrile copolymer/trimetylated silica) | 17.40 |
| Dimethicone//dimethicone PEG-10/15 crosspolymer | 2.00 |
| Lauryl PEG-9 polydimethylsiloxyethyl dimethicone | 1.00 |
| Dimethicone/vinyl dimethicone crosspolymer//methyl trimethicone | 1.50 |
| Pantethine | 0.50 |
| Tocopheryl acetate | 0.20 |
| Neopentyl glycol diethylhexanoate | 7.50 |
| Polydiethylsiloxane | 3.00 |
| Methyl trimethicone | 13.92 |
| Sorbitan sesquioleate | 0.01 |

Sunscreen Formula 8

This anhydrous formula, which contains the microsphere-entrapped zinc oxide of the present invention in combination with several organic sunscreen agents including Avobenzone, can be used to form a stick-form bronzer product.

| Components | wt % |
|---|---|
| Dipentaerythrityl hexahydroxystearate/stearate/rosinate | 1.50 |
| Bis-diglyceryl polyacyladipate-2 | 13.00 |
| Shea butter | 4.00 |
| Polyglyceryl-2 triisostearate | 6.00 |
| Butyloctyl salicylate | 4.00 |
| Dipentaerythrityl tetrabehenate/polyhydroxystearate// behenic acid//hydroxystearic acid | 5.00 |
| Microcrystalline wax | 5.00 |
| Avobenzone | 3.00 |
| Ethylhexyl salicylate | 5.00 |
| Homosalate | 5.00 |
| Polyester-8 | 3.00 |
| Tridecyl trimellitate | 5.00 |
| Polyethylene | 2.50 |
| Isononyl isononanoate | 1.00 |
| Diethylhexyl carbonate | 8.00 |
| Neopentyl glycol diheptanoate | 3.79 |
| Tricaprylin | 2.75 |
| Mica/iron oxides/titanium dioxide | 1.50 |
| Mica/iron oxides | 0.75 |
| Microsphere-entrapped ZnO (zinc oxide/diphenyl capryl methicone, polyvinylidene chloride/acrylonitrile copolymer/trimethylated silica) | 2.00 |
| Pentaerythrityl tetra-di-t-butyl hydroxyhydrocinnamte | 0.01 |
| Tocopheryl acetate | 0.10 |
| Simethicone | 0.10 |

Sunscreen Formula 9

This anhydrous formula, which contains the microsphere-entrapped zinc oxide of the present invention in combination with several organic sunscreen agents including Avobenzone, can be used to form a gel-type bronzer product.

| Components | wt % |
|---|---|
| Hydrogenated polyisobutene | 13.00 |
| Simethicone | 0.10 |
| VP/Eicosene copolymer | 7.00 |
| Dextrin palmitate | 11.00 |
| Hydrogenated polyisobutene | 22.50 |
| Dimethicone | 9.00 |
| Pentaerythrityl tetra-di-t-butyl hydroxyhydrocinnamte | 0.05 |
| Hydrogenated polyisobutene/ethylene/propylene/styrene copolymer/butylene/ethylene/styrene copolymer | 4.50 |
| Dipentaerythrityl hexahydroxystearate/hexastearate/hexarosinate | 1.08 |
| PPG-3 myristyl ether | 1.00 |
| Jojoba butter | 1.00 |
| Butyloctyl salicylate | 4.00 |
| Avobenzone | 3.00 |
| $C_{30}$-$C_{38}$ olefin/isopropyl maleate/MA copolymer | 1.00 |
| Tocopheryl acetate | 0.50 |
| Sweet almond oil | 1.00 |
| Calcium sodium borosilicate/iron oxides | 0.50 |
| Calcium sodium borosilicate/titanium dioxide/iron oxides | 1.50 |
| Mica/iron oxides | 1.50 |
| Ethylhexyl salicylate | 5.00 |
| Homosalate | 5.00 |
| Polyester-8 | 3.00 |
| Jojoba esters | 1.77 |
| Microsphere-entrapped ZnO (zinc oxide/diphenyl capryl methicone, polyvinylidene chloride/acrylonitrile copolymer/trimethylated silica) | 2.00 |

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

What we claim is:

1. A method for modifying or treating solid particles, comprising:
   (a) forming a gelled mixture by mixing either simultaneously or sequentially in any order (1) hollow microspheres each comprising a deformable polymeric shell having entrapped therein an expandable fluid, (2) a polar organic solvent capable of swelling but not dissolving the polymeric shells of the hollow microspheres, and (3) solid particles, wherein micro-channels are formed in the swelled polymer shells to allow entry of the solid particles into the hollow microspheres and exit of the expandable fluid therefrom, thereby forming microspheres that each comprises a collapsed polymeric shell in a gelled state and has one or more of said solid particles entrapped therein;
   (b) removing the expandable fluid and the polar organic solvent from the gelled mixture; wherein the expandable fluid is first removed from the gelled mixture by degassing at a reduced pressure or under vacuum conditions, followed by a quenching step in which water is added to the gelled mixture to allow separation of the microspheres from one another before removal of the polar organic solvent; and
   (c) coating the microspheres thus-produced with a film-forming material to form a liquid-impermeable membrane thereon.

2. The method of claim 1, wherein the polar organic solvent is selected from the group consisting of dimethylformamide, dimethylchloride, trichloroethylene, chloroform, methanol, ethanol, isopropanol, acetone, ethyl acetate, butyl acetate, and methyl ethyl ketone.

3. The method of claim 1, wherein the expandable fluid is selected from the group consisting of gases, air, nitrogen, volatile liquid hydrocarbons, isobutane, and isopentane.

4. The method of claim 1, wherein the collapsed microspheres have an average particle size ranging from about 1 micron to about 50 microns, and the solid particles have an average particle size ranging from about 0.001 micron to about 0.5 micron.

5. The method of claim 1, wherein the collapsed polymeric shell comprises at least one synthetic polymer obtained by polymerization of one or more ethylenically unsaturated monomers selected from the group consisting of vinylidene chloride, vinyl chloride, acrylonitrile, acrylic acid and its $C_1$-$C_{20}$ aliphatic or aromatic esters, methacrylic acid and its $C_1$-$C_{20}$ aliphatic or aromatic esters, acrylamide, methacrylamide, vinyl pyrrolidone, alkenes, styrene, ethylene, propylene, butylene, methylpentene, and 1,3-butadiene.

6. The method of claim 1, wherein the collapsed polymeric shell comprises at least one synthetic thermoplastic polymer selected from the group consisting of polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers thereof.

7. The method of claim 1, wherein the collapsed polymeric shell comprises a copolymer of vinylidene chloride, acrylonitrile, and/or methyl methacrylate.

8. The method of claim 1, wherein the entrapped solid particles comprise one or more materials selected from the group consisting of talc, kaolin, mica, bismuth oxychloride, chromium hydroxide, barium sulfate, polymethylmethacrylates (PMMA), boron nitride, nylon beads, polymeric powders, silica, silica beads, lakes, metal oxides, iron oxide, chromium oxide, zinc oxide, titanium dioxide, and physical and chemical sunscreen agents.

9. The method of claim 1, wherein the entrapped solid particles comprise one or more materials capable of generating free oxygen radicals.

10. The method of claim 8, wherein the entrapped solid particles comprise one or more metal oxides.

11. The method of claim 10, wherein the entrapped solid particles comprises titanium dioxide, zinc oxide, or a combination thereof.

12. The method of claim 1, wherein the liquid-impermeable membrane comprises one or more materials selected from the group consisting of acrylate homo- or co-polymers, methacrylate homo- or co-polymers, vinylpyrrolidone homo- or co-polymers, silicone gums, silicone waxes, silicone oils, silicone resins, esters, hydrocarbons, celluloses, fatty acids, fatty alcohols, and inorganic materials.

13. The method of claim 12, wherein the liquid-impermeable membrane comprises crosslinked dimethicone or trimethylated silica treated with dimethyl siloxane.

14. The method of claim 9, wherein the entrapped solid particles further comprise at least one organic compound susceptible to oxidative decomposition or degradation.

15. The method of claim 14, wherein said at least one organic compound is at least one organic sunscreen agent susceptible to oxidative decomposition or degradation.

16. The method of claim 14, wherein said at least one organic compound is an organic dye susceptible to oxidative decomposition or degradation.

17. The method of claim 15, wherein the at least one organic sunscreen agent is selected from the group consisting of 4,4'-t-butyl methoxydibenzoylmethane, 2-ethylhexyl-2-cyano-3,3-diphenylacrylate, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethylhexyloxy)-2-hydroxyl-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)]aminobenzoate, n-hexyl 2-(4-diethylamine-2-hydroxybenzoyl)benzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof.

18. The method of claim 17, wherein the at least one organic sunscreen agent is 4,4'-t-butyl methoxydibenzoylmethane.

19. The method of claim 15, wherein the at least one organic sunscreen agent further comprises a second organic sunscreen agent.

20. The method of claim 15, wherein the at least one organic sunscreen agent is encapsulated in protective structures.

21. The method of claim 20, wherein the protective structures comprise additional microspheres with collapsed polymeric shells, into which the at least organic sunscreen agent is entrapped.

22. The method of claim 1, wherein at least some of the collapsed microspheres have titanium dioxide particles entrapped therein.

23. The method of claim 1, wherein at least some of the collapsed microspheres have zinc oxide particles entrapped therein.

24. The method of claim 1, wherein some of the collapsed microspheres have titanium dioxide particles entrapped therein, and others have zinc oxide particles entrapped therein.

25. The method of claim 1, wherein said collapsed microspheres contain one or more antioxidants co-entrapped with the solid particles inside the collapsed polymeric shell of each microsphere or coated over the microspheres.

* * * * *